(12) United States Patent
Carter, Jr. et al.

(10) Patent No.: US 9,488,555 B2
(45) Date of Patent: Nov. 8, 2016

(54) METHOD FOR OPTIMIZING VERTICAL PROBE ALIGNMENT USING DIAGNOSTIC MIXING ROUTINES

(75) Inventors: Richard Henry Carter, Jr., Merion Station, PA (US); William David Dunfee, Newark, DE (US); Media Marie Lloyd, Elkton, MD (US); John P. Mizzer, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 351 days.

(21) Appl. No.: 14/009,853

(22) PCT Filed: Apr. 6, 2012

(86) PCT No.: PCT/US2012/032505
§ 371 (c)(1),
(2), (4) Date: Oct. 4, 2013

(87) PCT Pub. No.: WO2013/106027
PCT Pub. Date: Jul. 18, 2013

(65) Prior Publication Data
US 2014/0024133 A1   Jan. 23, 2014

Related U.S. Application Data

(60) Provisional application No. 61/473,630, filed on Apr. 8, 2011.

(51) Int. Cl.
*G01N 1/38* (2006.01)
*B01F 11/00* (2006.01)
*B01F 15/00* (2006.01)
*G01N 35/10* (2006.01)

(52) U.S. Cl.
CPC ............. *G01N 1/38* (2013.01); *B01F 11/0085* (2013.01); *B01F 15/00253* (2013.01); *B01F 15/00331* (2013.01); *G01N 35/1011* (2013.01); *G01N 2035/1058* (2013.01); *Y10T 436/25* (2015.01)

(58) Field of Classification Search
CPC ........................................................ G01N 1/38
USPC ........................................................... 436/174
See application file for complete search history.

(56) References Cited

U.S. PATENT DOCUMENTS

| | | | |
|---|---|---|---|
| 6,382,827 B1 | 5/2002 | Gebrian | |
| 7,258,480 B2 * | 8/2007 | Dunfee | B01F 11/0085 366/197 |
| 7,284,900 B2 | 10/2007 | Mayer | |

FOREIGN PATENT DOCUMENTS

| | | |
|---|---|---|
| DE | 297 17 607 U1 | 2/1999 |
| EP | 1 321 756 A1 | 6/2003 |
| JP | H07 220162 A | 8/1995 |

OTHER PUBLICATIONS

PCT International Search Report and Written Opinion dated Jun. 20, 2012 (7 Pages).
Extended European Search Report dated Sep. 4, 2014 of corresponding European Patent Application No. 12864735.1, 5 Pages.

* cited by examiner

*Primary Examiner* — Christopher A Hixson
*Assistant Examiner* — Emily Berkeley

(57) ABSTRACT

A method and apparatus for adjusting the height of a tip of a mixing element, such as a needle probe, compares the mixing efficiency observed at two heights separated by a predetermined distance. The heights can be incrementally adjusted to determine the location of the bottom of a mixing vessel and, by extension, the approximate location for placing the mixing element for efficient mixing of solutions in the mixing vessel.

16 Claims, 18 Drawing Sheets

320

| | | | | | | |
|---|---|---|---|---|---|---|
| | DECISION MATRIX | | | | | |
| AB | 1 | 0 | -1 | -1 | -1 | -1 |
| BC | 1 | 1 | 1 | 0 | -1 | -1 |
| CD | 1 | 1 | 1 | 1 | 0 | -1 |

| ACTION | LOWER | A | A-B | B | B-C | C | HIGHER |
|---|---|---|---|---|---|---|---|

METHOD FOR OPTIMIZING VERTICAL PROBE ALIGNMENT USING DIAGNOSTIC MIXING ROUTINES

CROSS-REFERENCE TO RELATED APPLICATIONS

This application claims priority to U.S. provisional application Ser. No. 61/473,630 filed Apr. 8, 2011, which is incorporated herein by reference in its entirety.

TECHNOLOGY FIELD

The present invention relates in general to alignment procedures for use with diagnostic equipment and, more particularly, to an alignment method and apparatus for uniformly mixing liquid samples, reagents, or other solutions in a container. Embodiments of the present invention are particularly well suited, but in no way limited, to providing an improved method for vertically aligning a mixing device for rapidly and uniformly mixing a liquid solution in a reaction vessel.

BACKGROUND

Various types of analytical tests related to patient diagnosis and therapy can be performed by analysis of a liquid sample taken from a patient's bodily fluids, or abscesses. These assays are typically conducted with automated clinical analyzers onto which tubes or vials containing patient samples have been loaded. The analyzer extracts a liquid sample from the vial and combines the sample with various reagents in special reaction cuvettes or tubes (referred to generally as reaction vessels). Usually the sample-reagent solution is incubated or otherwise processed before being analyzed. Analytical measurements are often performed using a beam of interrogating radiation interacting with the sample-reagent combination, for example, turbidimetric, fluorometric, absorption readings, or the like. The measurements allow determination of end-point or rate values from which an amount of analyte related to the health of the patient may be determined using well-known calibration techniques.

Clinical chemistry analyzers employ many different processes to identify analytes and, throughout these processes, patient liquid samples and samples in combination with various other liquids (such as reagents, diluents, or re-hydrated compositions) are frequently required to be mixed to a high degree of uniformity. Due to increasing pressures on clinical laboratories to increase analytical sensitivity, there continues to be a need for improvements in the overall processing efficiency of clinical analyzers. In particular, sample analysis continuously needs to be more effective in terms of increasing assay throughput. There remains a need for sample-reagent mixers that mix a liquid solution to a high degree of uniformity at very high speed without unduly increasing analyzer cost or requiring a disproportional amount of time or space.

Various methods have historically been implemented to provide a uniform sample solution mixture including agitation, stirring/mixing, ball milling, etc. One popular approach involves using a pipette to alternately aspirate and release a portion of liquid solution within a liquid container. Magnetic mixing, in which a vortex mixing action is introduced into a solution of liquid sample and liquid or non-dissolving reagents, has also been particularly useful in clinical and laboratory devices.

U.S. Pat. No. 6,382,827 discloses a method for mixing a liquid solution contained in a liquid container by causing a freely disposed, spherical mixing member to rapidly oscillate within the solution in a generally circular pattern within the container. The spherical mixing member is caused to rapidly move within the solution by revolving a magnetic field at high speed in a generally circular pattern in proximity to the liquid container. Magnetic forces acting upon the magnetic mixing member cause it to generate a mixing motion within the liquid solution.

U.S. Pat. No. 7,258,480, assigned to the assignee of the present application and incorporated herein by reference, discloses a mixing device for mixing solutions within a biochemical analyzer by moving a sampling probe needle in a two-dimensional, generally parabolic or generally "boomerang-shaped" mixing pattern of the probe needle.

Methods that rely on a mechanical stirring motion, such as that disclosed in U.S. Pat. No. 7,258,480, can be sensitive to the vertical location of the stirring element. For example, when placed too high relative to the bottom of the cuvette (or other reaction vessel), the stirring element will not stir the solution efficiently, requiring more time and motion or causing an incomplete mixture. Likewise, when placed too low relative to the bottom of the cuvette, the stirring element can impact the bottom or any sloped sides of the cuvette or otherwise become stuck or damped, and provide an ineffective or failed mix. However, many apparatus that use mechanical stirring to mix a solution rely on either a fixed height for a stirring element, which may be changed when a mixing element (e.g., a probe needle) is installed, or they require a manual estimation of the height of the tip of the stirring element. Such approaches may be prone to mechanical failure or operator error.

Thus, there continues to be a need for an improved approach to the design of a simplified, space-efficient, liquid sample and/or sample-reagent mixer. In particular, there is a continuing need for an improved sample-reagent solution mixer with a reliable means for adjusting the height of the mixing element, such that the mixer provides high speed and mixing of solutions contained in reaction vessels with a very high degree of uniformity in a desirably small amount of time and space.

SUMMARY

Embodiments of the present invention address and overcome the above shortcomings and drawbacks by providing a method and apparatus for incrementally adjusting the height of a mixing element. Incremental adjustment of the mixing element, in accordance with the methods, allows the height of the mixing element to be set at an optimal position to provide the maximum mixing efficiency possible for the mixing element and vessel. This technology is particularly well-suited for, but by no means limited to, chemical analyzers.

Embodiments of the present invention are directed to a method for adjusting a mixing element comprising positioning the mixing element at a first vertical position in a first vessel. The method further includes performing a first mixing test to determine a first value corresponding to the effectiveness of mixing at the first vertical position. The method further includes positioning the mixing element at a second vertical position in a first vessel. The method further includes performing a second mixing test to determine a second value corresponding to the effectiveness of mixing at the second vertical position. The method further includes comparing the first and second values to determine if the bottom of the mixing vessel is generally below the first vertical position, above the second vertical position, or between the first and second vertical positions.

According to one aspect of the invention, the first and second vertical positions are separated by a predetermined step size.

According to another aspect of the invention, adjusting a mixing element further comprises adjusting at least one of the first or second vertical positions and repeating at least one additional mixing test until the comparing step indicates that the bottom of the mixing vessel is between the first and second vertical positions.

According to yet another aspect of the invention, the method for adjusting a mixing element further comprises adjusting at least one of the first or second vertical positions in response to the comparing step, such that at least one vertical position is adjusted upward by a first increment if the bottom of the vessel is above the second vertical position and adjusted downward by a second increment if the bottom of the vessel is below the first vertical position. In some embodiments, both the first and second vertical positions are adjusted. In some embodiments, the adjusting step is repeated until an approximation of the vertical position of the mixing vessel is determined. In some embodiments, wherein the adjusting step is repeated, the method further comprises positioning the mixing element at a third vertical position for mixing reagents during normal operation, wherein the third vertical position is a predetermined vertical offset above the approximate location of the vertical position of the bottom. In some embodiments, wherein the adjusting step is repeated, the first and second increments are fixed values. In some embodiments, wherein the adjusting step is repeated, the first and second increments vary in magnitude in response to the comparing step. In some embodiments, wherein the first and second increments vary in magnitude in response to the comparing step, the first and second increments are reduced after successive comparing steps.

According to one aspect of the invention, at least one of the first and second mixing tests in the method comprise the step of mixing a first solution with a mixing element for a first predetermined time to create a first mixed state. At least one of the first and second mixing tests further comprises measuring a property of the first mixed state. At least one of the first and second mixing tests further comprises further mixing the first solution with the mixing element for a second predetermined time to create a second mixed state. At least one of the first and second mixing tests further comprises measuring a property of the second mixed state. At least one of the first and second mixing tests further comprises comparing the measurements of the first and second mixed states. According to some embodiments of the invention, comparing the measurements of the first and second mixed states further includes determining a ratio of a first measured value corresponding to the first state to a second measured value corresponding to the second state. In another embodiment, the comparing step further includes determining if the ratio exceeds a threshold value. According to another embodiment of the invention, at least the combination of the first and second predetermined time is great enough to mix the first solution to a substantially complete mixed state when the mixing element is at a vertical position conducive to normal operation.

According to another aspect of the invention, at least one of the first and second mixing tests comprises the step of mixing a first solution with a mixing element for a first predetermined time to create a first mixed state. At least one of the first and second mixing tests further comprises the step of measuring a property of the first mixed state. At least one of the first and second mixing tests further comprises the step of further mixing the first solution with another mixing element that has been previously calibrated for a second predetermined time to create a second mixed state. At least one of the first and second mixing tests further comprises the step of measuring a property of the second mixed state. At least one of the first and second mixing tests further comprises the step of comparing the measurements of the first and second mixed states.

According to another aspect of the invention, comparing the first and second values further includes determining if the bottom of the first vessel is generally near the first or second vertical positions.

Other embodiments of the present invention are directed to a method for adjusting a mixing element comprising positioning the mixing element at a first vertical position in a first vessel. The method further includes depositing a first plurality of reagents in the first vessel in a substantially unmixed state. The method further includes moving the mixing element, during a first mixing step, in a horizontal mixing pattern to create a first mixed state of the first plurality of reagents. The method further includes measuring a first value of a property of the first mixed state of the first plurality of reagents. The method further includes performing a second mixing step, whereby the first plurality of reagents are further mixed to create a first substantially mixed state. The method further includes measuring a second value of a property of the first substantially mixed state. The method further includes comparing the first and second values corresponding to the first plurality of reagents to create a first result to determine the effectiveness of the first mixing step when the mixing element is at the first vertical position. The method further includes positioning the mixing element at a second vertical position in a second vessel, which may be the same as the first vessel. The method further includes depositing a second plurality of reagents in the second vessel in a substantially unmixed state. The method further includes moving the mixing element, during a third mixing step, in a horizontal mixing pattern to create a first mixed state of the second plurality of reagents. The method further includes measuring a first value of a property of the first mixed state of the second plurality of reagents. The method further includes performing a fourth mixing step, whereby the second plurality of reagents are further mixed to create a second substantially mixed state. The method further includes measuring a second value of a property of the second substantially mixed state. The method further includes comparing the first and second values corresponding to the second plurality of reagents to create a second result to determine the effectiveness of the third mixing step when the mixing element is at the second vertical position. The method further includes comparing the first and second results to determine if the second position is substantially more effective than the first.

According to one aspect of the invention, the method further comprises adjusting the first and second vertical positions in response to the step of the first and second results. According to one aspect of the invention, the method also further comprises repeating the step of positioning the mixing element at a first vertical position in a first vessel and all steps through and including adjusting the first and second vertical positions in response to the step of the first and second results, until an approximate vertical position of the bottom of the vessel has been determined. According to one aspect of the invention, these steps further comprise applying a predetermined vertical offset to the approximate vertical position of the bottom of the vessel during normal operation of a mixing process.

Other embodiments of the present invention are directed to non-transitory computer-readable media holding software instructions for positioning a mixing element at a first vertical position and performing a first mixing test to determine a first mixing value at the first vertical position. The instructions also include positioning the mixing element at a second vertical position that is a predetermined amount above the first vertical position and performing a second mixing test to determine a second mixing value at the second vertical position. The instructions further compare the first and second mixing values to determine if a bottom of one or more vessels is generally, at the first vertical position, below the first vertical position, above the second vertical position, or between the first and second vertical positions.

According to one aspect of the invention, software instructions position the mixing element at a third vertical position that is a predetermined amount above the second vertical position, perform a third mixing test to determine a third mixing value at the third vertical position, position the mixing element at a fourth vertical position that is a predetermined amount above the third vertical position, and perform a fourth mixing test to determine a fourth mixing value at the fourth vertical position. The comparison includes determining if the bottom of the one or more vessels is generally 1) below the first (lowest) vertical position, 2) above the fourth (highest) vertical position, 3) at the first, second, or third vertical position, or 4) between any combination of the tested vertical positions. The spatial relationship between test positions constrains the possible outcomes and influences the final conclusions that can be reached. The comparison also uses the spatial relation among positions to provide a test of the integrity of any individual determinations by identifying when that errant result does not make physical sense within the defined arrangement of probe positions relative to the bottom of the vessel established by the overall comparison of known results.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 15 is a logical decision matrix used with some embodiments of the method of FIG. 12;

FIG. 17 is a logical mapping of the expected results determined by the spatial relations among all the combinations of various positions of the bottom of a vessel versus the various positions of a probe needle that may be tested when using certain embodiments of the method of FIG. 12.

DETAILED DESCRIPTION OF ILLUSTRATIVE EMBODIMENTS

The above problems in the prior art have motivated the discovery of improved apparatus and methods for reliably and/or automatically aligning the vertical placement of a probe within a vessel containing fluids for a solution. By aligning the height, the probe can mix the solution efficiently and consistently during normal use of the chemical analyzer.

Figure 1:
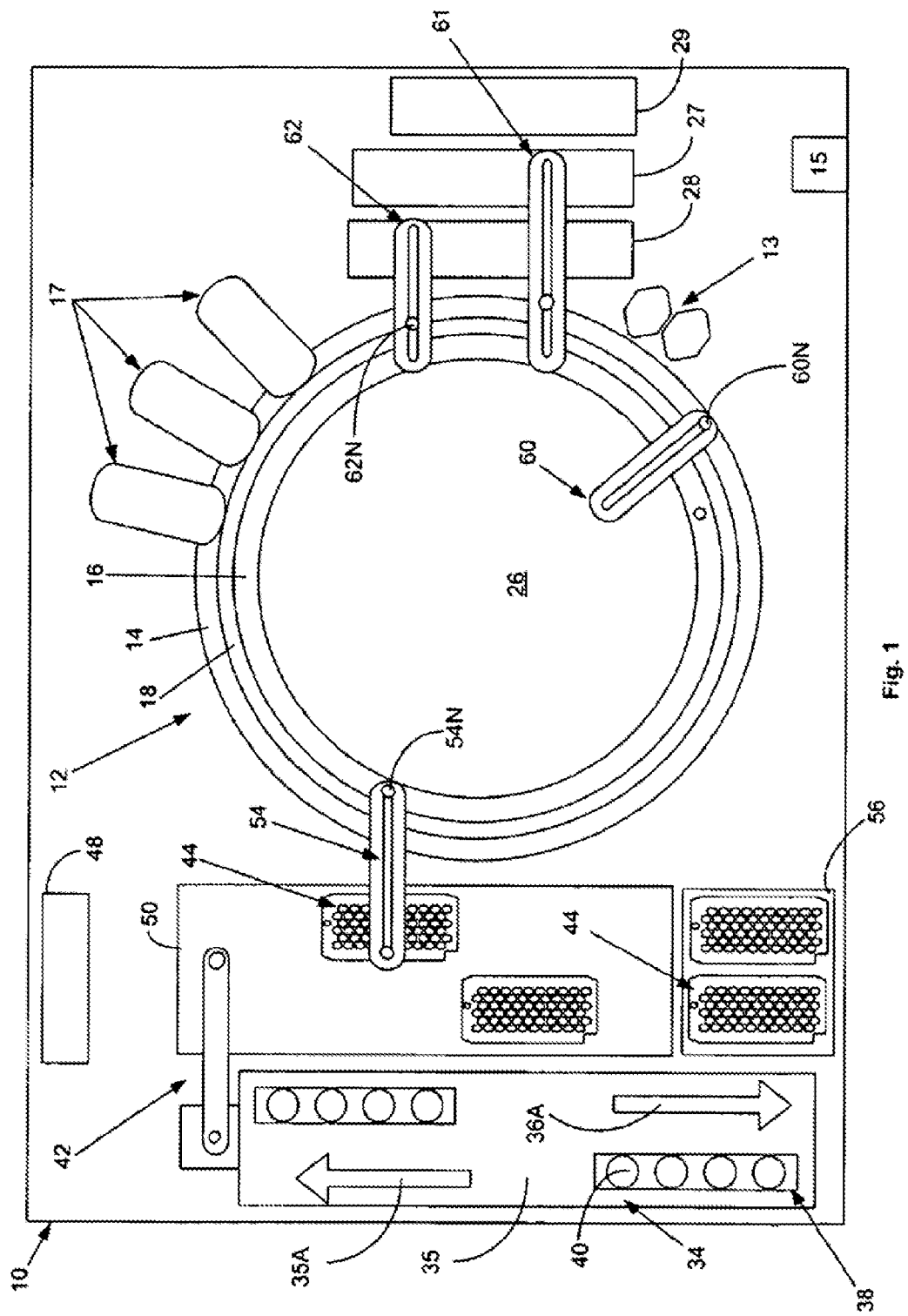
FIG. 1 is a top view of an exemplary chemical analyzer in which embodiments of the vertical alignment and mixing method and apparatus may be employed.
Figure 2:
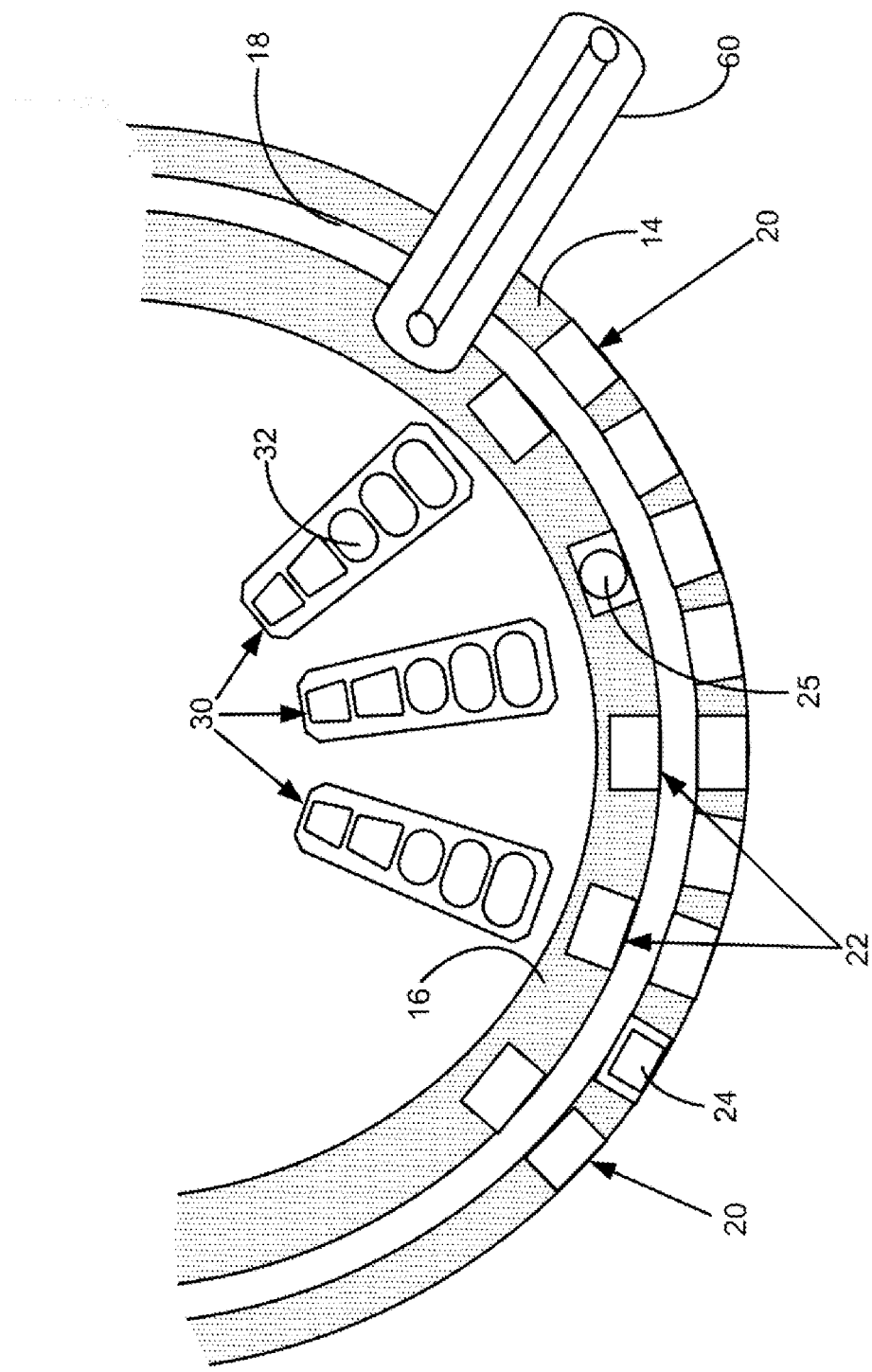
FIG. 2 is a top view of a portion of a carousel for transporting reaction vessels and cuvettes for use with certain embodiments.

FIG. 1, taken with FIG. 2, shows schematically the elements of an automatic chemical analyzer 10 in which the present invention may be advantageously practiced, which may include, for instance the chemical analyzer described in U.S. Pat. No. 7,258,480. Analyzer 10 comprises a reaction carousel 12 supporting an outer carousel 14 having cuvette ports 20 formed therein and an inner carousel 16 having vessel ports 22 formed therein, the outer carousel 14 and inner carousel 16 being separated by an open groove 18.

Figure 2B:
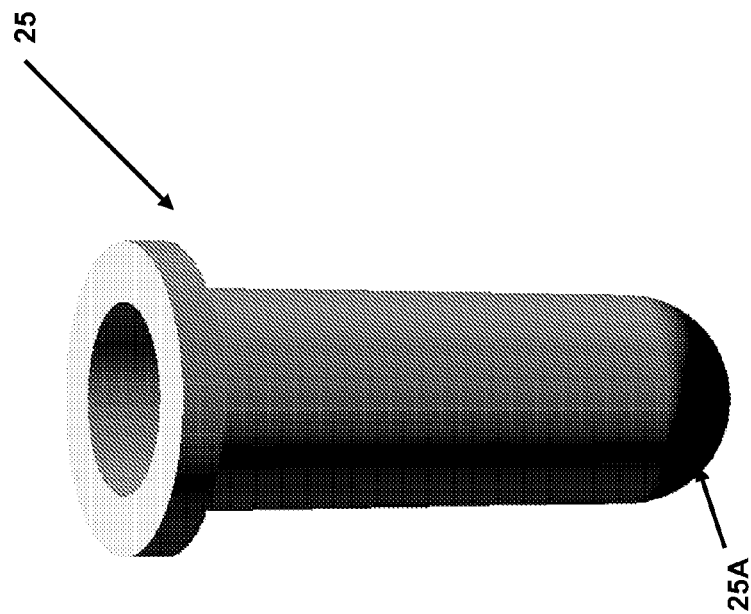
FIG. 2B is a perspective view of another type of reaction vessel for use with certain embodiments.
Figure 2A:
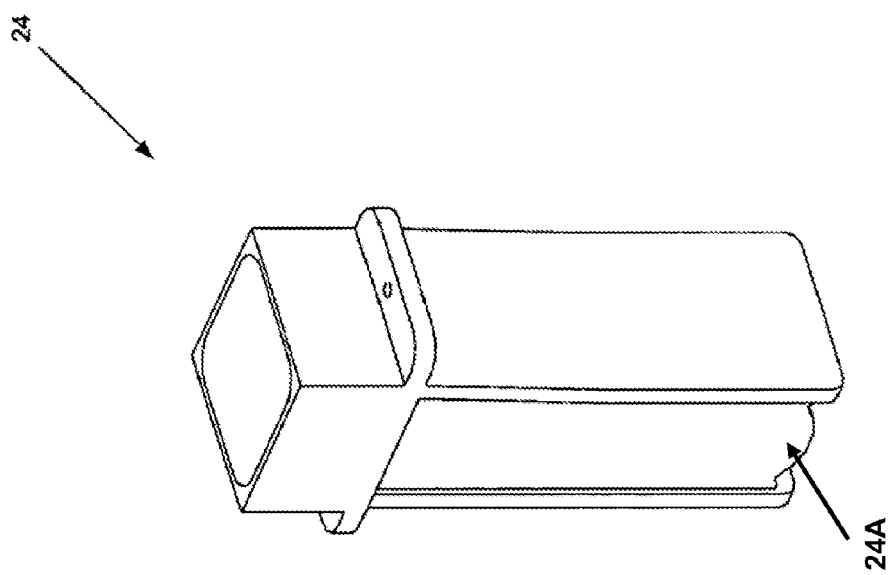
FIG. 2A is a perspective view of a cuvette for use with certain embodiments.

Cuvette ports 20 are adapted to receive a plurality of reaction cuvettes 24, as seen in FIG. 2A, that contain various reagents and sample liquids for conventional clinical and immunoassay assays. Vessel ports 22 can be adapted to receive a plurality of reaction vessels 25, as shown in FIG. 2B, that contain specialized reagents for ultra-high sensitivity luminescent immunoassays. Cuvettes 24 and reaction vessels 25 can include bottom portions 24A and 25A, respectively. While cuvettes and reaction vessels can have differing shapes, as used herein, the methods for mixing can be applied to the contents of reaction vessels 25 or cuvettes 24, and the terms reaction vessels and cuvettes should be considered broadly and interchangeably. Reaction vessels can include, for instance, cuvettes, vials, tubes, or other suitable vessels for mixing reagents and solutions.

Reaction carousel 12 is rotatable using stepwise movements in a constant direction, the stepwise movements being separated by a constant dwell time during which reaction carousel 12 remains stationary and computer controlled assay operational devices 13, such as sensors, reagent add stations, mixing stations, and the like, operate as needed on an assay mixture contained within a cuvette 24.

Analyzer 10 is controlled by software executed by a computer 15 based on computer programs written in a machine language like that used on the Dimension® clinical chemistry analyzer sold by Siemens Healthcare Diagnostics Inc. of Deerfield, Ill., and widely used by those skilled in the art of computer-based electromechanical control programming. Computer 15 also executes application software programs, such as the Dimension Vista® system software for performing assays conducted by various analyzing means 17 (e.g., detection units) within analyzer 10. Analyzing means can include, for instance, one or more photometers, turbidimeters, nephelometers, electrodes, electromagnets, and/or LOCI® readers for interpreting the results of reactions within the reaction vessels or cuvettes. It should be understood that each of the steps described herein can be performed directly by, or in response to, programming instructions executed on one or more processor(s), such as computer 15, available to analyzer 10. These software instructions can be stored for execution via any conventional means including a hard drive, solid state memory, optical disk, flash memory, or the like.

As seen in FIG. 1, a bi-directional incoming and outgoing sample fluid tube transport system 34 comprises a mechanism for transporting sample fluid tube racks 38 containing open sample fluid containers such as sample fluid tubes 40 from a rack input load position at a first end of the input lane 35 to the second end of input lane 35 as indicated by open arrow 35A. Liquid specimens contained in sample tubes 40 are identified by reading bar coded indicia placed thereon using a conventional bar code reader to determine, among other items, a patient's identity, tests to be performed, if a sample aliquot is to be retained within analyzer 10, and, if so, for what period of time. It is also common practice to place bar coded indicia on sample tube racks 38 and employ a large number of bar code readers installed throughout analyzer 10 to ascertain, control, and track the location of sample tubes 40 and sample tube racks 38.

A conventional liquid sampling probe 42 is located proximate the second end of the input lane 35 and is operable to aspirate aliquot portions of sample fluid from sample fluid tubes 40 and to dispense an aliquot portion of the sample fluid into one or more of a plurality of vessels in aliquot vessel array 44. This provides a quantity of sample fluid to facilitate assays and to provide for a sample fluid aliquot to be retained by analyzer 10 within an environmental chamber 48. After sample fluid is aspirated from all sample fluid tubes 40 on a rack 38 and dispensed into aliquot vessels in array 44 and maintained in an aliquot vessel array storage and transport system 50, rack 38 may be moved, as indicated by open arrow 36A, to a front area of analyzer 10 accessible to an operator so that racks 38 may be unloaded from analyzer 10.

Sample aspiration probe 54 is controlled by computer 15 and is adapted to aspirate a controlled amount of sample from individual aliquot vessels in array 44 positioned at a sampling location within a track (not shown) and is then shuttled to a dispensing location where an appropriate amount of aspirated sample is dispensed into one or more cuvettes 24 for testing by analyzer 10 for one or more analytes. After sample has been dispensed into reaction cuvettes 24, conventional transfer means move aliquot vessel arrays 44, as required, within aliquot vessel array storage and dispensing module 56 between aliquot vessel array transport system 50, environmental chamber 48, and a disposal area (not shown).

Temperature-controlled storage areas or servers 26, 27, and 28, contain an inventory of multi-compartment elongate reagent cartridges 30 loaded into the system via input tray 29, such as those described in U.S. Pat. No. 6,943,030 assigned to the assignee of the present invention, containing reagents in wells 32 perform a number of different assays. Reagents may be moved and aligned within analyzer 10 by any conventional means, including those described in 2009P13675WO, also assigned to the assignee of the present invention, and incorporated herein by reference. Computer 15 can control and track the motion and placement of the reagent cartridges 30. Reagents from server 26, 27, and 28 can be handled by one or more reagent probe arms, 60, 61, and 62.

Figure 3:
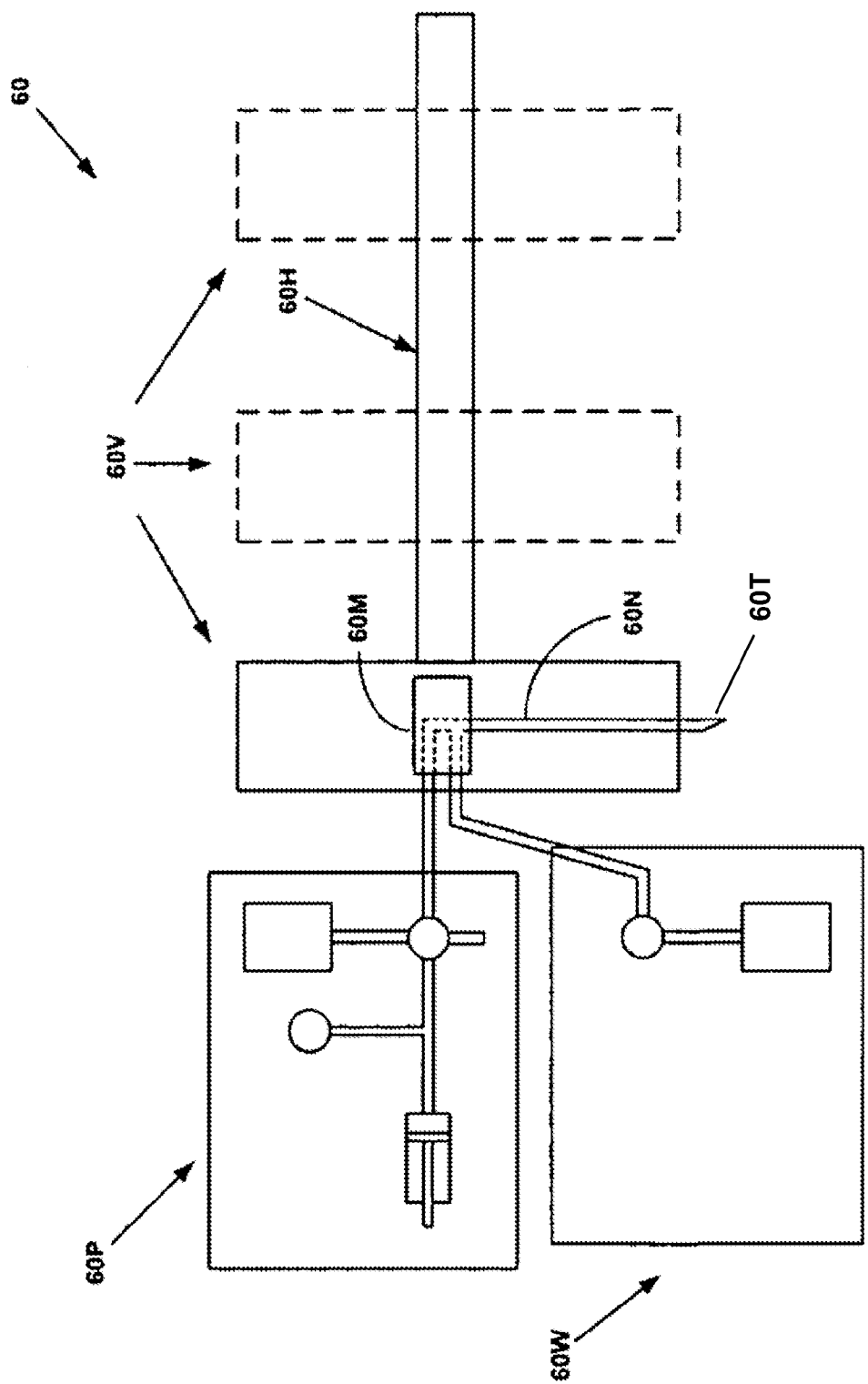
FIG. 3 is a system view of control mechanisms for controlling the motion and use of a probe needle for use with certain embodiments.

Reagent aspiration probe 60, which is useful in performing the present invention, may be seen in FIG. 3 as comprising a horizontal drive component 60H, a vertical drive component 60V, a wash module component 60W, a pump module component 60P, an aspiration and dispensing probe needle 60N, which may include a tapered needle tip 60T designed to puncture the covering of reagent cartridge 30, and a wash manifold component 60M having the primary functions described in Table 1 below. Components of the wash module component 60W and pump module component 60P identified in FIG. 3 will be described below. Horizontal drive component 60H and vertical drive component 60V are typically computer controlled stepper motors or linear actuators and are controlled by computer 15 for providing precisely controlled movements of the horizontal drive component 60H and vertical drive component 60V.

TABLE 1

| Module | Primary Functions |
| --- | --- |
| Horizontal Drive 60H | Position the vertical drive 60V over reagent cartridges 30 containing reagent liquids and over cuvettes 24 carried in ports 20. |
| Vertical Drive 60V | Drive probe 60N through the covering of a reagent cartridge 30 for aspiration of reagents and place the tip 60T into cuvettes 24 for dispensing of reagents and mixing. |
| Wash Module 60W | Remove contamination from probe tip 60T with liquid cleansing solutions. |
| Wash Manifold 60M | Connect probe tip 60T to pump module 60P. |
| Pump Module 60P | Pump reagent liquids and sample fluids. |
| Probe Needle 60N | Aspirate and dispense reagent liquids and sample fluids. |

Figure 4:
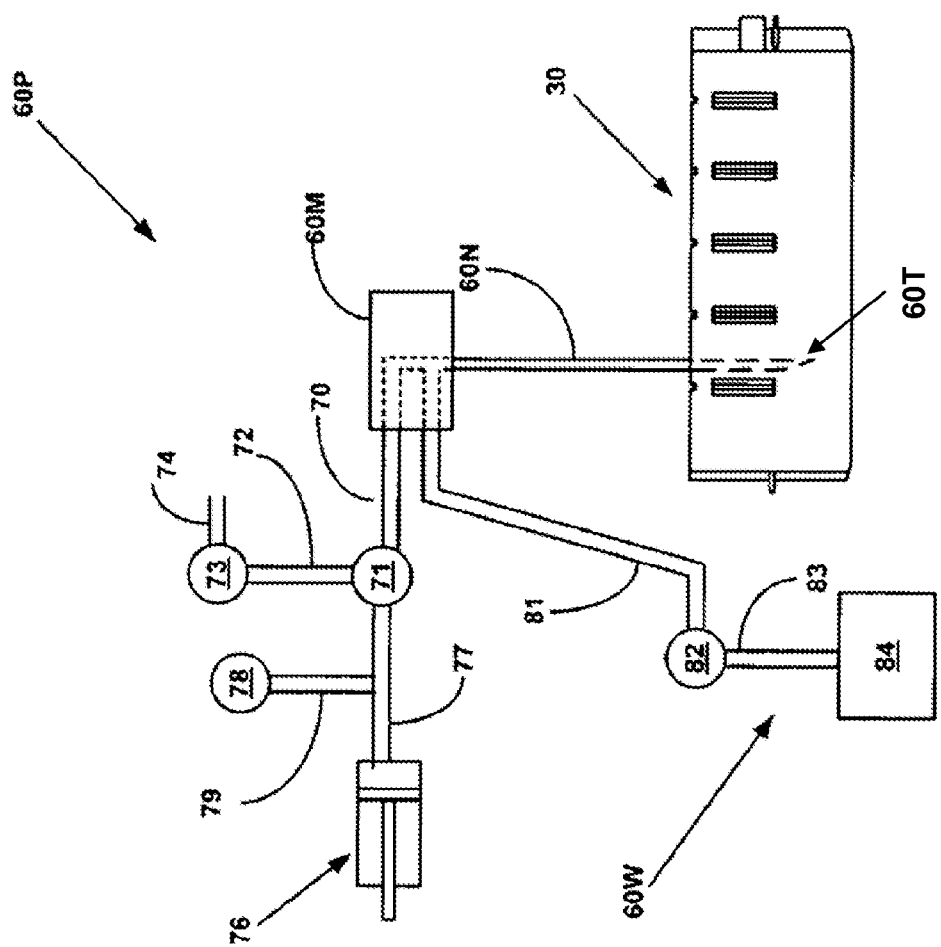
FIG. 4 is a system view of control mechanisms for controlling the motion and use of a probe needle for use with certain embodiments.

FIG. 4 shows pump module 60P connected to a conventional, hollow, liquid-carrying probe 60N having conventionally defined interior and exterior surfaces and supported by wash manifold 60M, the wash manifold 60M being connected by a hollow air tube 70 to a three-way valve 71. Probe needle 60N may be connected to wash manifold 60M using any of several screw-like connectors, clips, or, alternately, permanently affixed or welded thereto. Valve 71 is operable to optionally connect air tube 70 to (1) a vent valve 73 connected to an atmospheric vent tube 74, or (2) a piston-type syringe pump 76 by a hollow air tube 77. A conventional air pressure measuring transducer 78 is connected to air tube 77 between pump 76 and valve 71 by a hollow air tube 79.

Figure 5:
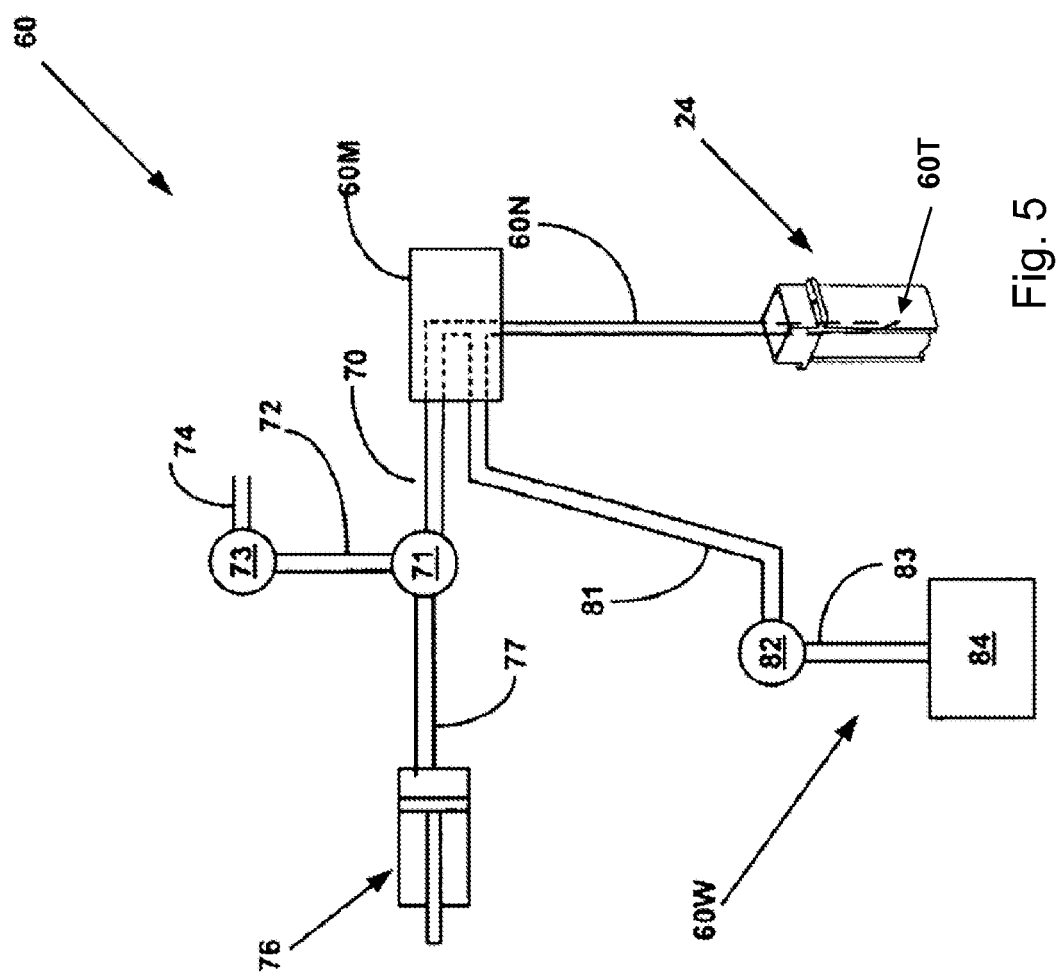
FIG. 5 is a system view of control mechanisms for controlling the motion and use of a probe needle for use with certain embodiments.

FIG. 4 also illustrates probe tip 60T and needle 60N having punctured the covering of a reagent carrier 30 and positioned within a reagent liquid contained therein. Level sensing means (for example, using well known capacitive signals) may be advantageously employed in order to ensure that probe needle 60N is in fluid communication with the liquid. Piston 76 is activated and the distance it is moved is controlled by computer 15 so that a controlled volume of reagent liquid is withdrawn or aspirated into probe needle 60N. During this process, valve 71 is closed to vent tube 72, but is open to air tube 77 and air tube 70. Valve 71 is operable to optionally connect air tube 70 to an optional vent valve 73 connected to an atmospheric vent tube 74. FIG. 4 also shows an optional wash manifold 60W as comprising a flush valve 82 connected to wash manifold 60W by a hollow liquid carrying tube 81. Flush valve 82 is operable to connect liquid carrying tube 81 to a pressurized rinse water source 84, which may contain water or any other suitable cleaner, by a hollow liquid tube 83. After aspiration of calibration or quality control liquid from reagent carrier 30 is completed, wash manifold 60M is raised by vertical drive 60V and positioned by horizontal drive 60H so that probe 60N may dispense calibration or quality control liquid into a cuvette 24 carried in port 20 in carousel 14 as illustrated in FIG. 5.

During operation of analyzer 10 using the devices illustrated in FIGS. 2-5, there are several instances when it is desirable or critical that liquids or solutions of one or more liquids be quickly and uniformly mixed, producing a demand for a mixing device that mixes a liquid or liquid solution to a high degree of uniformity at very high speed, without unduly increasing analyzer cost or requiring a disproportional amount of space or time or a specialized mixing-only device.

High speed mixing to obtain a uniformly dispersed solution might be required, for example:

1. After reagent aspiration probe 60 extracts a first reagent from a first reagent cartridge 30 and dispenses reagent into a reaction cuvette 24;

2. Before sample aspiration probe 54 extracts sample from a vessel in aliquot vessel array 44 and dispenses sample into a reaction cuvette 24, a roller mixing assembly (not shown) may be operated to cause needle 54N to mix sample that has been retained in vessel array 44 for an extended period of time waiting re-testing or additional testing; or 3. After sample aspiration probe 54 delivers sample into a reaction cuvette 24;

4. After reagent aspiration probe 60 extracts a second reagent from a second reagent cartridge 30 and dispenses reagent into reaction cuvette 24.

Probe assemblies that can be used to mix samples can include a first or second reagent probe for adding first or second reagents, an aliquotter probe for transferring specimen from a vial to the aliquot array 44, a probe for transferring specimen amongst aliquot vessels in array 44, such as for diluting samples, or a sample probe for transferring specimen from an aliquot vessel array 44 to a reaction vessel 25 or cuvette 24. Typically, probe assemblies 42 and 54 are sample aspiration probes and probe assemblies 60, 61, and 62 are reagent aspiration probes. The probes are not limited to these functions, however, and more general terminology may be used herein such as "sampling probes" to describe various types of probe assemblies.

Figure 6:
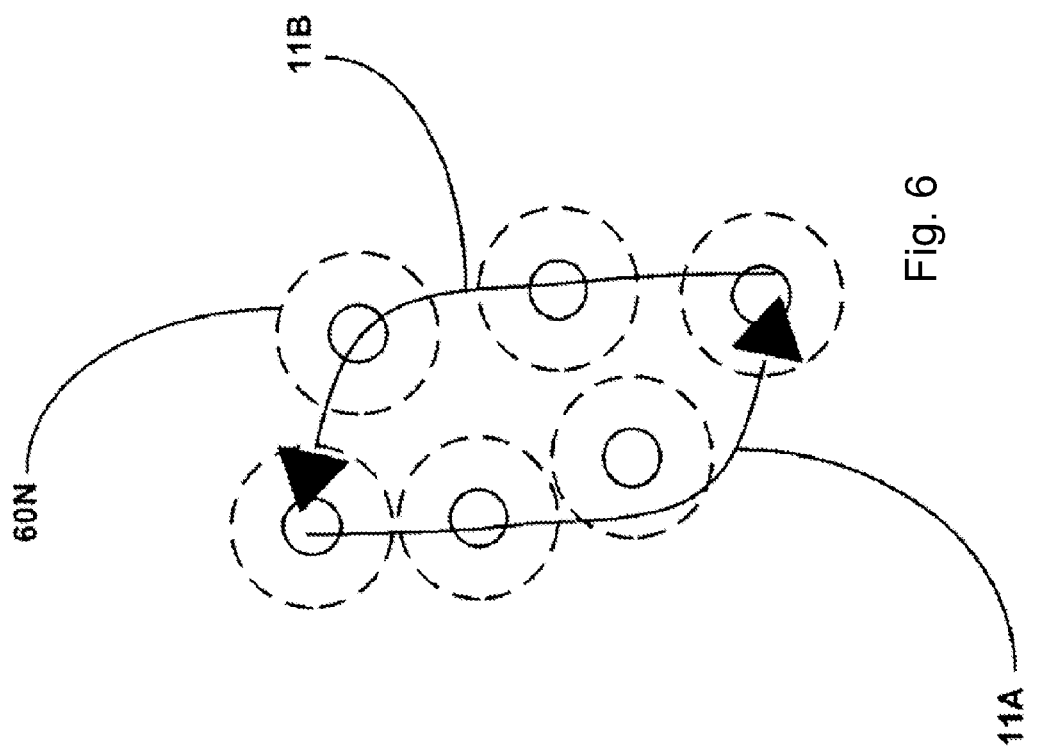
FIG. 6 is a time-lapse cutaway view showing a motion pattern for a probe needle during a mixing operation in accordance with some embodiments.

Mixing methods can provide a stirring motion, for instance, moving a sampling probe needle in a linear mixing pattern, a circular mixing pattern, an elliptical mixing pattern, or any other pattern described herein. It is desirable to use mixing processes that produce about a 97% degree of solution uniformity or more, that are completed in an amount of time less than about 500 milliseconds, and that do not generate non-uniformities like bubbles or foam within the solution. The mixing pattern may also move the sampling probe needle 60N, 54N, or 62N (FIG. 1), in a two-dimensional, generally parabolic or generally "boomerang-shaped" mixing pattern like that disclosed in U.S. Pat. No. 7,258,480, as shown in FIG. 6. In this configuration, probe 60N is moved in the horizontal plane within cuvette 24 in pattern 11A, 11B, or both.

Figure 7:
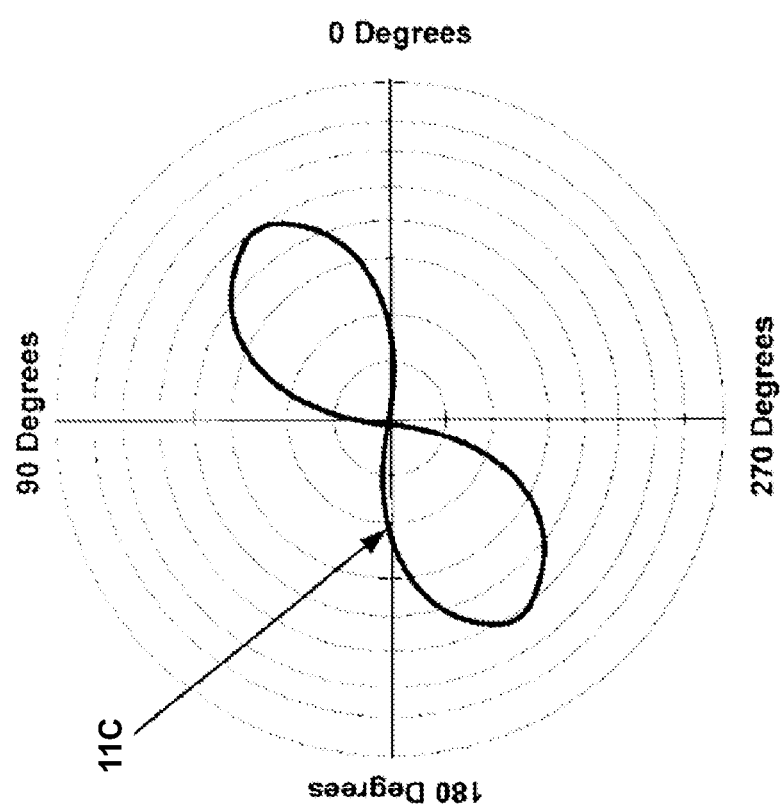
FIG. 7 is a two-dimensional plot showing a motion pattern for a probe needle during a mixing operation in accordance with some embodiments.
Figure 8:
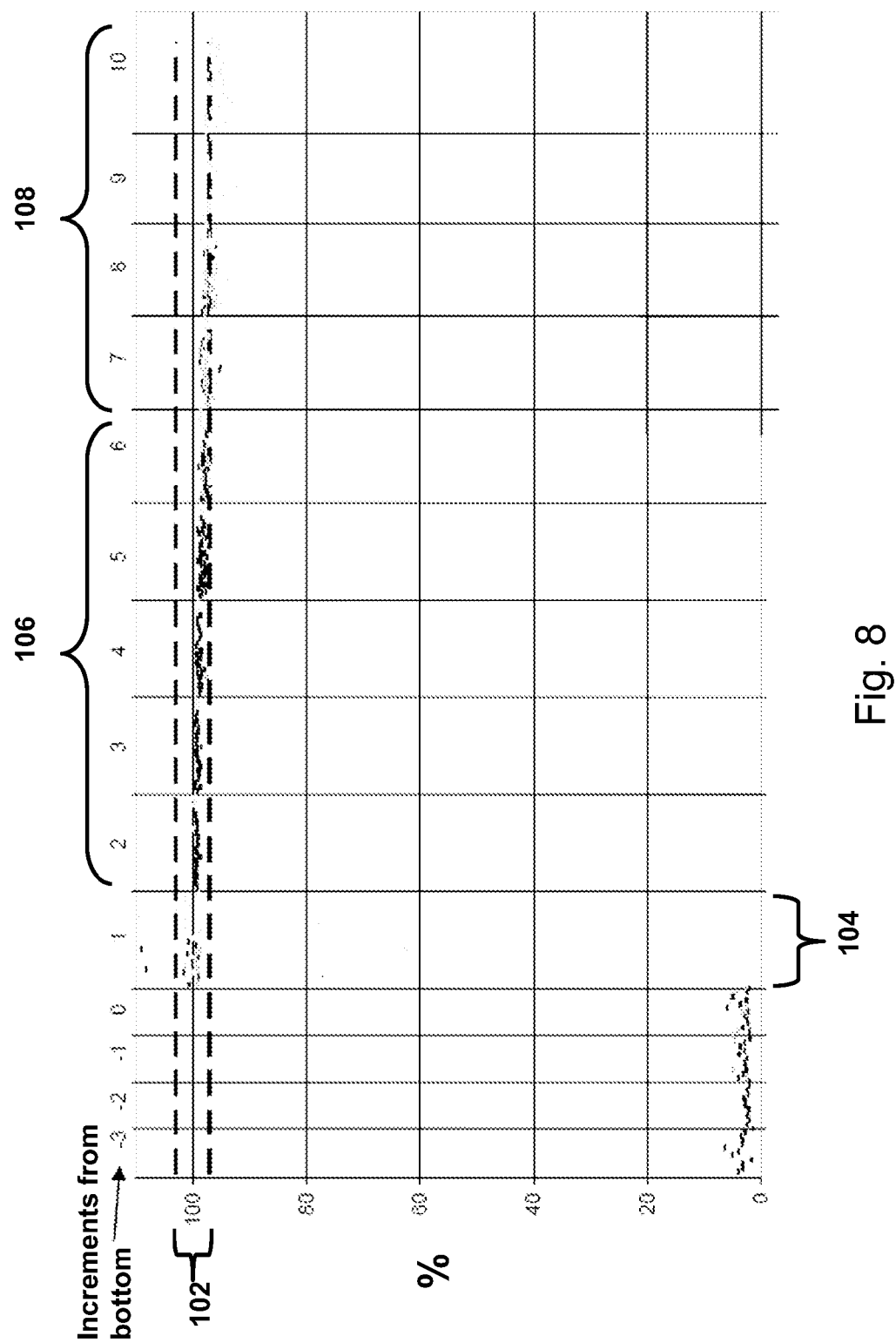
FIG. 8 is a two-axis plot showing experimental results of mixing efficiency vs. vertical placement of a probe needle tip.

Another mixing pattern that may be suitable, includes rapidly moving probe tips 60T in a "figure-8" or "lemniscate-shaped" mixing pattern 11C, like that disclosed in 2009P13675WO and illustrated in FIG. 7, within sample retained in vessels in aliquot vessel array 44, or within sample-reagent mixture in cuvette 24 after the dispensing process illustrated in FIG. 5.

Typical mixing patterns can include a mixing pattern 11A-C that moves the probe tip 60T in a horizontal pattern that has a range of about 1.7 mm to about 2.6 mm. While this range is suitable for motion when the probe tip 60T is in the middle or upper portion of cuvette 24, when the tip 60T is near the bottom of the cuvette 24, the horizontal motion may cause the probe tip 60T to impact any curved bottom features 24A of the cuvette 24. It will be appreciated that each probe, such as sampling probe needle 60N, 54N, or 62N, can be made to move in any appropriate mixing pattern, as chosen for the application by using mechanisms shown in FIG. 3. Sampling probe 60 is used herein as an illustration.

The position of the tip 60T of the sampling probe needle can be controlled in three dimensions by horizontal and vertical drive mechanisms 60H and 60V, respectively. These drive mechanisms can include translating devices in any suitable coordinate system, such as X-Y-Z, as suitable for the application. For example, drive mechanisms 60H and 60V may include electromechanical devices, including motors, piezo-electric drivers, linear or rotational actuators, or pneumatic or hydraulic devices such as pistons and the like. The motion may be further controlled by any number of conventional means, including gears, levers, tracks, grooves, hinges, magnetic or electric field devices, belts, pulleys, chains, springs, and the like. In some embodiments, the drive mechanisms 60H and 60V are controlled by computer 15, allowing the position, velocity, acceleration, and/or jerk to be controlled.

In some embodiments, vertical drive mechanism 60V can operate independently from horizontal drive mechanism 60H. This allows the probe needle tip 60T to be inserted, retracted, or otherwise positioned once the horizontal location (e.g., X-Y) has been determined. (As used herein, two orthogonal horizontal dimensions can be referred to as the X-Y dimensions and the vertical direction can be referred to as the Z direction.) Vertical drive mechanism 60V can include a linear translation device, such as a linear actuator, hydraulic or pneumatic device, or a belt or rack/pinion driven arm. In some embodiments, an accurate or precise location of some portion of the body of needle 60N may be determined by encoding within the vertical drive mechanism 60V. For example, optical, friction, or gear based encoders can determine a repeatable location in the Z dimension of the base of needle 60N, such as a location within the manifold 60M. This encoding allows repeatable positioning of the tip 60T of the probe needle 60N. In some embodiments, the vertical drive mechanism 60V is capable of incremental vertical positioning of the probe needle with a step size suitable for the size of the cuvette 24 or reaction vessel 25, such as a step-size of about 0.167 mm.

The exact location of the probe needle tip 60T may be configurable. For example, in embodiments where probe needle 60N is replaceable or removable, a mechanical offset, such as a set screw, may allow probe tip 60T to be adjustable relative to the vertical location of manifold 60M. Adjustments may be made by a technician at the time of probe needle installation, during a repair or calibration stage (such as when repairing or replacing parts, including transfer arms), or during troubleshooting of mixing problems. The procedures can be used, along with similar procedures to calibrate the horizontal (e.g., X-Y) alignment of the probe. In addition, it will be understood that this procedure can be used in horizontal directions to calibrate the position of the probe tip in a horizontal dimension to find an optimal or suitable mixing position in any direction.

During a calibration stage, the location of the probe needle tip 60T relative to the bottom 24A of cuvettes 24 (secured in the cuvette ports 20 in reaction carousel 12) is determined. A determination of this location allows the tip 60T to be placed at a height that maximizes mixer efficiency. FIG. 8 shows experimental results of the mixing efficiency for various probe tip heights. Using a vertical step size of about 0.167 mm, it can be seen that when the tip 60T is lowered to the level of cuvette 24, or lower, the mixing efficiency is negligible. When the tip 60T impacts the bottom 24A of the cuvette 24, any mixing motion is damped or prevented, resulting in virtually no mixing by the probe 60N. When compared to a properly mixed sample, and expressed as a percentage, the solution can be said to be ~0% mixed. This establishes a lower threshold when the solution in the cuvette 24 is said to have a mixture failure.

In contrast, the goal for proper mixture is in the range 102, which is where the amount of mixing during a single time period, such as about 0.5 sec., is approximately equal to the amount of mixing in a properly mixed cuvette 24, which can be determined by placing the probe needle tip 60T at a height above the bottom 24A and mixing for two time periods, such as about 1.0 sec. The ideal range 102 can include threshold values, such as 95%. It should be appreciated that a height value below 0 does not mean that the tip 60T has necessarily damaged or pierced the bottom 24A of the cuvette 24. In some embodiments, vertical drive mechanism 60V includes an override mechanism that prevents moving the needle 60N further when it encounters resistance above a threshold. Appropriate mechanisms such as torque limiting devices, clutches, and the like will be readily available to a person of ordinary skill in the art.

As the tip 60T is raised so that it is no longer interfering with the bottom of the cuvette 24, at position 104 (e.g., 1 step above the bottom of the cuvette, which may be considered a bottom position of the cuvette), it can be seen that mixture efficiency improves. As can be seen, raising the tip a single increment above the bottom of the cuvette can greatly improve mixing results, including many samples mixing in the acceptable range 102. However, due to variation in height, the shape of the cuvette, and/or mechanical play in the drive systems 60H and 60V or carousel 12, results when the probe needle tip 60T is a single increment above the cuvette bottom 24A (or 25A, when mixing in a reaction vessel 25) are inconsistent, with some samples only being partially mixed, such as those samples being mixed when the probe needle tip 60T impacts sloped sides of the reaction vessel 25A or cuvette bottom 24A.

When tip 60T is moved higher than the transition ranged 104, to position 106, it can be seen that the mixing efficiency is ideal and consistent for several successive increments. Height range 106 is the target height of the probe needle tip 60T during operation. The apparatus and methods disclosed herein can be useful in locating this range 106 or, more specifically, locating the transition height 104, such that using a predetermined number of increments offset will place the probe needle tip 60T in ideal height range 106.

As the probe needle tip 60T is raised above the ideal range 106 into height range 108, which in the illustrated embodiment starts 7 increments above the cuvette bottom 24A or reaction vessel bottom 25A, the mixing efficiency tapers off. As the tip 60T height becomes substantially greater than the bottom 24A of the cuvette 24 (or the bottom 25A of the reaction vessel 25), the amount of sample below the tip 60T increases. This portion of the sample is not directly mixed or stirred by the probe needle 60N and, instead, relies on turbulence and viscosity of the solution to mix it. Therefore, it is ideal to find the optimal height range 106 of the probe needle tip 60T to ensure repeatable and efficient mixing of the cuvette 24 or reaction vessel 25 contents.

From FIG. 8, it can be seen that if a controller, such as computer 15, that controls vertical drive mechanism 60V can determine the vertical location of the bottom 24A of cuvette 24, the controller can set the height of the tip 60T at a predetermined offset during mixing operations to ensure that mixing is conducted efficiently. In the example shown in FIG. 8, if the vertical location of transition step 104 can be determined, the height of tip 60T can be incremented a predetermined number of steps, such as 1-6, and the tip 60T will be operating in the ideal height range 106, such that mixing efficiency is roughly 100%, as shown by band 102. In some embodiments, this predetermined offset is roughly about 1 mm. It will be appreciated that the offset can be expressed in step-wise increments, such as 6 units, or can be a predetermined distance, such as 1 mm, depending on the type of vertical drive mechanism 60V that is used.

Figure 9:
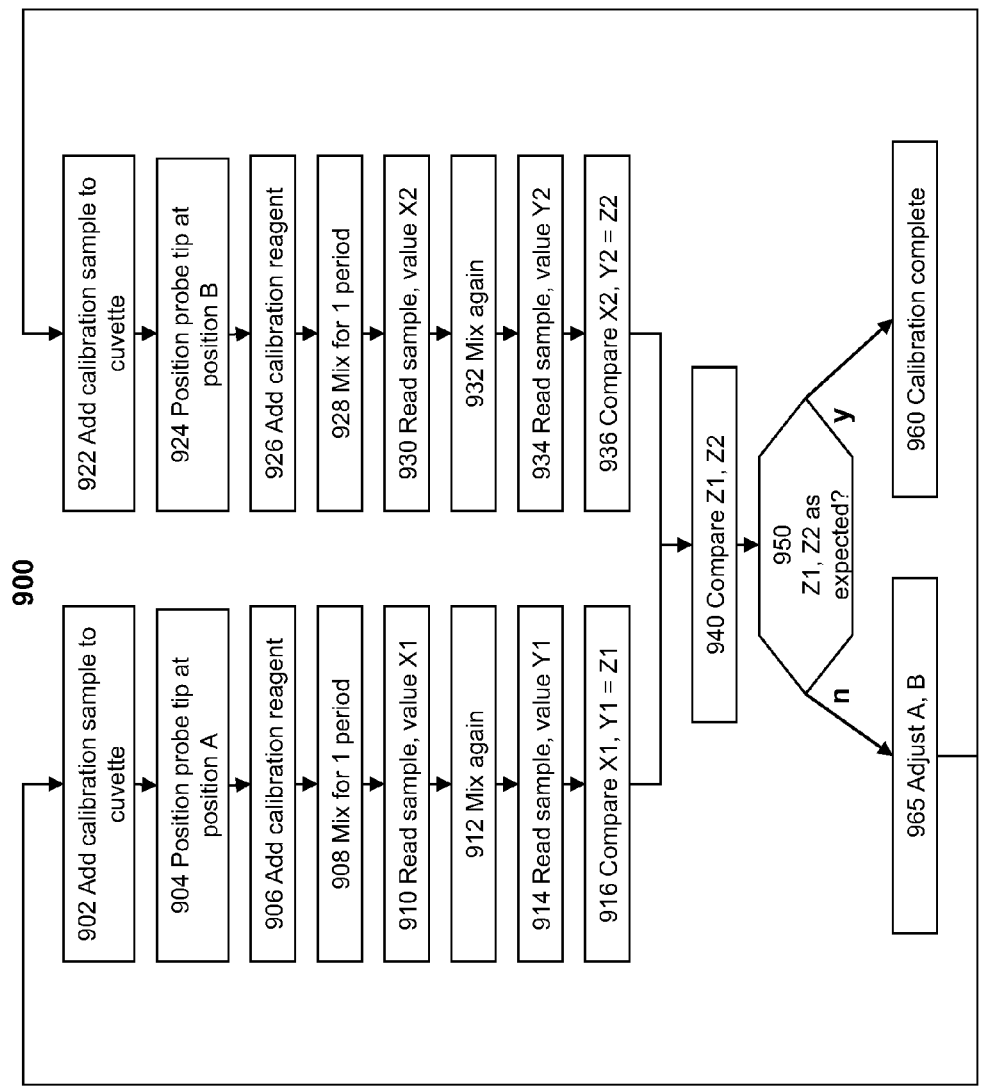
FIG. 9 is a flow chart showing an embodiment of the process for determining the proper alignment height of the tip of a probe needle.
Figure 10:
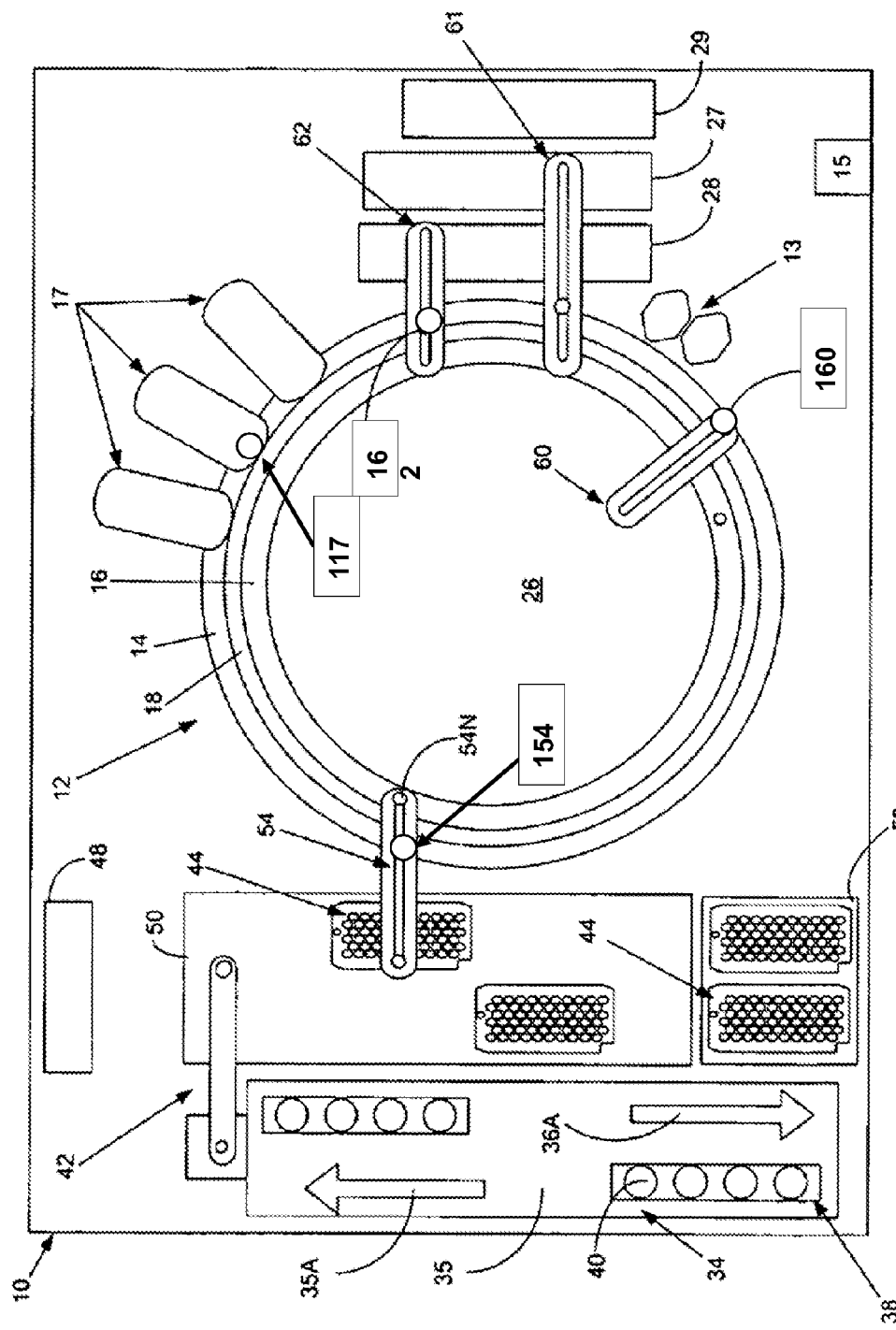
FIG. 10 is a top view of an exemplary chemical analyzer, including exemplary placement locations, in which certain steps of an exemplary mixing method may be performed.

The height of the tip 60T that matched the bottom of cuvette 24 can be determined using the following method 900, shown in FIG. 9. At step 902, a calibration sample is prepared in cuvette 24. In some embodiments, this sample can include a known quantity of distilled water or other inert sample. This sample can be prepared, for example, by transferring a calibration aliquot from aliquot array 44 via arm 54 when the cuvette 24 is located at position 154, as illustrated in FIG. 10. At step 904, carousel 12 rotates to place cuvette 24 in a location accessible to probe needle 60N (labeled in FIG. 1), such as position 160 (FIG. 10). Probe needle 60N is then positioned at a first height position A, which may initially be the expected height of the bottom 24A. At step 906, an aliquot of a calibration reagent is dispensed into the cuvette 24. In some embodiments, this reagent is a dye, which can be prepared in reagent cartridges 30. It will be appreciated that the dispensing step 906 can occur before the positioning step 904, in some embodiments.

At step 908, the solution components in the cuvette 24 are mixed. This step can include moving the probe needle 60N via any conventional mixing pattern discussed herein, such as by controlling horizontal drive mechanism 60H via computer 15. This mixing step can be performed for a first predetermined time interval, such as 0.5 sec. In some embodiments, the time interval selected is the same mixing interval that would be used during normal operation of the chemical analyzer 10, which allows testing of whether mixing will be complete during normal operation.

At step 910, cuvette 24 is moved via carousel 12 to a position, such as 117 (FIG. 10), where one of sensors 17 can observe the cuvette 24. In some embodiments, a photometer is used to determine how much light is absorbed or scattered by the calibration reagent, such as a dye. This result is the value X1, which is a function of the amount of dispersal of the calibration reagent in the cuvette 24. In some embodiments, value X1 indicates the level of light that is absorbed by the dye using a laser tuned to an absorption wavelength of the dye. Value X1 can be indicative of the efficiency or effectiveness of mixing the sample at position A.

At step 912, cuvette 24 is moved to a position accessible to a probe needle for additional mixing. This position can be back to position 160 for mixing by probe 60N or to position 162 (FIG. 10), for instance, for mixing by another probe needle, such as 62N (labeled in FIG. 1). By placing cuvette 24 at a different probe, such as 62N, the sample can be mixed via a previously calibrated probe. If the mixing step 912 is performed by the same probe 60N as the first mixing step 908, the height of the probe can be increased to a level where the controller 15, or the operator, is confident that the tip 60T is not interfering with the bottom 24A. In some embodiments, the second mixing step 912 is performed for a longer interval, such as about 1.0 sec., to ensure that the solution is fully mixed during this step.

At step 914, the cuvette 24 is again moved to a position to be read by a sensor, such as 17, as explained with respect to step 910. The resulting measurement gives a value Y1. Value X1 can be indicative of the efficiency or effectiveness of mixing the sample at position A.

At step 916, Y1 and X1 are compared. By taking a ratio of X1:Y1, or performing any other comparative operation, such as subtraction, a comparative value Z1 can be created. Using a ratio allows a percentage of mixing completion to be calculated. If the probe needle tip 60T was not interfering with the bottom 24A, such as at height 106, this ratio Z1 will be ideally close to 100%. If, instead, the tip 60T was pressed into bottom 24A, such as at a height less than 104, the ratio will be very low, such as 0%. If, instead, the tip 60T was near the bottom 24A such that the tip occasionally interfered with the bottom, such as at a height 104, the ratio could be a value anywhere in the range of 0%-100%. If, instead, the tip 60T was too high relative to the bottom 24A, such as at a height in range 108, the ratio will be high, but may be below the ideal range 106. This can allow a determination of where the probe tip 60T is relative to the bottom 24A during step 916, at least to the extent that it indicates whether height position A is below height 106.

Steps 922-936 are the same as steps 902-916, respectively. In steps 922, a fresh solution is used, which may either be in the same cuvette 24, after a washing/cleaning step, or in a separate, fresh cuvette. The second cuvette and solution are handled the same way as cuvette 24 in steps 904-916. At 924, a calibration reagent such as a dye is added. At step 926, the tip 60T is positioned in the second cuvette for mixing. However, whereas at step 906, the tip 60T was positioned at a first height, at step 926, the tip 60T is placed at a different height position B, which is a predetermined offset from height A, for reasons that will become clear. In some embodiments, the offset between A and B is a single step-wise height increment, while in other embodiments, the offset may initially be several step-wise increments for a first iteration of the calibration steps, which can be used as a coarse adjustment step. In some embodiments, the A-B offset can be reduced in future passes, while in other embodiments, it can remain the same.

At step 928, the solution in the second cuvette is mixed by probe needle 60N. At step 930, the quality of the mix is measured, producing first value X2, as explained in step 910. At step 932, the solution in the second cuvette is again mixed to ensure complete mixture, as explained in accordance with step 912. At step 934, the result of the second mixing step is measured, producing value Y2, as explained with respect to step 914. At step 936, the measurements X2 and Y2 are compared in the way explained with respect to step 916. This can allow a determination of where the probe tip 60T is relative to the bottom during step 926, at least to the extent that it indicates whether height position B is below height 106.

At step 940, values Z1 and Z2 are compared to determine the difference, if any, between mixing at height A and height B. This can include determining if any difference is larger or smaller than a threshold value.

At step 950, computer 15 or operator applies rules to determine if values Z1 and Z2 are consistent with locating the bottom, as explained herein. If the values are as expected, then the controller 15 or operator completes the calibration process. Upon completion, the height of the bottom of cuvette 24 is located. An offset, such as about 1 mm, or a predetermined number of height steps, such as 1-6, can be added to the height of the bottom and used as the height of probe tip 60T during subsequent normal operation.

At step 965, where Z1 and Z2 are not as expected, an adjustment to A and B can be made, and the steps 902-950 can be repeated until the expected values of Z1 and Z2 are obtained. The basic logic behind the adjustment at step 965 can be understood with respect to FIG. 11.

Figure 11:
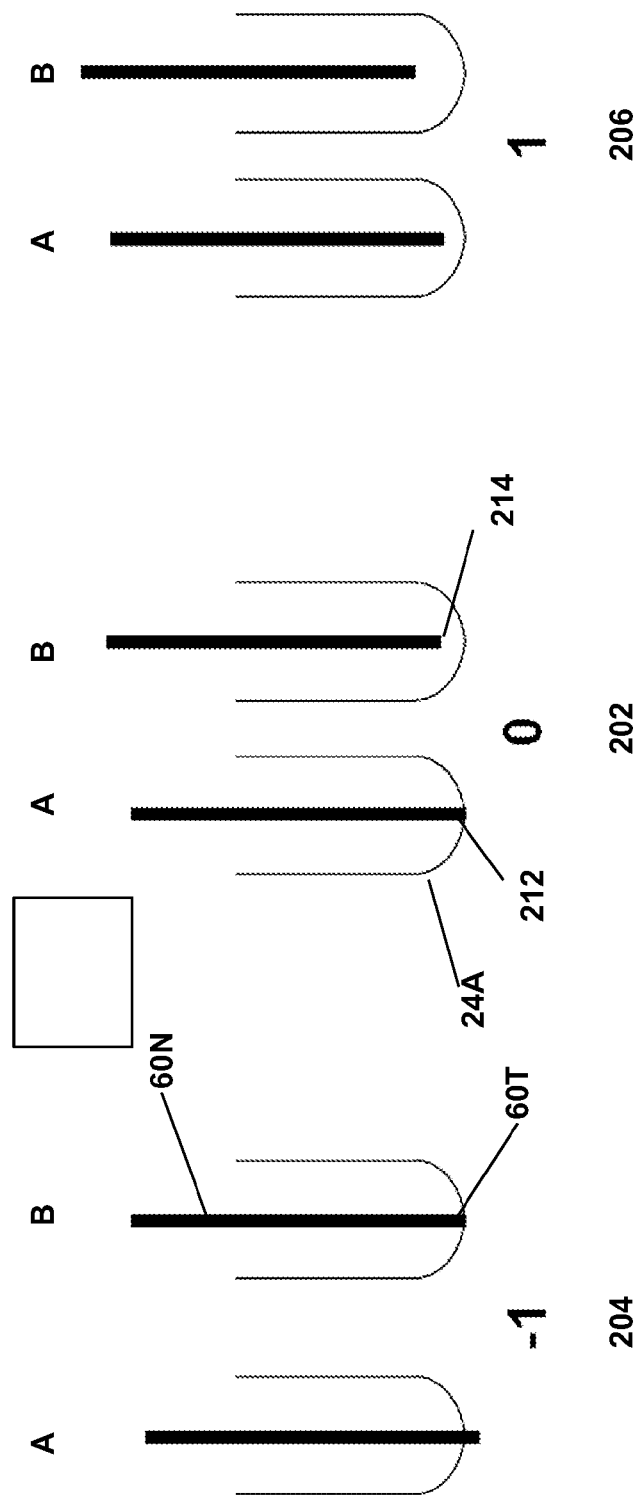
FIG. 11 is an illustrative side view of various possible probe states that may be observed during execution of an exemplary mixing method.

FIG. 11 shows three possible scenarios that can be detected by observing mixing results Z1 and Z2. In scenario 202, position A, at 212, impacts the bottom 24A of cuvette 24, while position B, at 214, is at a height sufficient to mix the sample. Scenario 202 occurs when the height is calibrated and the height of the bottom 24A has been located. In this scenario, Z1 will reflect a failed mix, such as revealing a mix that is below a threshold, such as 25%. Meanwhile, Z2 will reflect a complete mix that exceeds a threshold, such as 85%. The result of observing Z1 and Z2 indicates that positions A and B are at heights 212 and 214 respectively, and no adjustment is needed. Needle probe tip 60T will be at an ideal operating height by adding a predetermined offset to position 212 during normal operation of chemical analyzer 10.

In scenario 204, both positions A and B impact bottom 24A, such that Z1 and Z2 will both be below a threshold, such as 15%. This result can be assigned a value −1, which indicates that the height of the tip 60T must be adjusted upward. In some embodiments, the incremental adjustment is the same for both A and B, and in some embodiments the adjustment is two vertical steps, as the Z-value for the initial position B has already been determined.

In scenario 206, neither position A nor B impacts bottom 24A, and Z1 and Z2 will both be substantially complete and above a threshold, such as 85%. This result can be assigned a value +1, which indicates that the height of the tip 60T must be adjusted downward. In some embodiments, the incremental adjustment is the same for both A and B, and in some embodiments the adjustment is two vertical steps, as the Z-value for the initial position B has already been determined.

It will be appreciated that if the values of Z1 and Z2 are stored in memory in computer 15, the successive pass of method 900 can either skip steps 922-936, or include these steps, such that Z-values for four positions A0, B0, A1, and B1 are determined. These Z-values can then be compared to find an adjacent pair of Z-values that correspond to positions 212 and 214, as shown in scenario 202.

In general, process 900 can be repeated such that at each step 950, the Z-values are compared to determine which state, (−1, 0, or 1) 204, 202, or 206 the current pass indicates. If the state is −1, 204, then the A and B heights are incremented upward and process 900 repeats. If the state is 1, 206, then the A and B heights are incremented downward and process 900 repeats. The process repeats until the adjacent A and B positions result in state 0, 202.

In some embodiments, the increment used for adjusting A and B can be the same, while in others, A and B can be adjusted at different step sizes. In some embodiments, the step-size can change between cycles. For example, a coarse search can be initially used where, if at step 950, a + or −1 state (206, 204) is detected, a first adjustment is made at step 965, where the first step size is larger than the minimum step size increment. This larger increment can be used until a successive pass of process 900 results in a transition of state (e.g., from −1 to +1). In response to a state transition, determined at step 950, at step 965, a smaller step size can be used for successive iterations of process 900 until state 0 (202) is achieved using a desired resolution.

In some embodiments, each step of process 900 is performed by or at the control of software running on computer 15. In other embodiments, one or more steps can be performed manually, such as by or at the control of a technician. In some embodiments, software running on computer 15 and the technician work together, such as via prompts asking for permission by the software, or by requests made by the technician.

Process 900 can be repeated for multiple probes, 54, 62, 60, 61, or the like. This allows any probe that will be used in a mixing process to be optimized. In addition, process 900 can be repeated serially, or in parallel with cuvettes located at different positions on carousel 12, to account for any variation in height of the cuvettes in the carousel or other variation(s). An average result for bottom position 212 can be used for determining the average bottom height before adding an offset to reach the approximate ideal mixing vertical position. In some embodiments, each probe to be used with a carousel can be calibrated by testing cuvettes at several positions on the carousel by rotating the carousel. The mixing efficiency for each height position can be determined by averaging the results for a height position for each of the positions tested around the cuvette carousel. Each height position can be tested by either raising/lowering the probe tip or lowering/raising the cuvette.

It should also be understood that cuvettes in carousels may not move directly between the locations 154, 117, 162, and 160, as there may be several dozen cuvettes in the carousel and the rotational step may be any distance. Therefore, the carousel may make several rotations before cuvette 24 travels from mixing position 160 to reading position 117, for instance.

In addition, the multiple iterations of steps 902-950 can be performed before a single adjustment is performed, such as by comparing the results of 3-5 cuvettes 24 or measurements on a single cuvette 24 before performing an adjustment to the height positions A or B. This embodiment may result in more reliable adjustment, particularly where the height A is already close to bottom 24A.

Figure 12:
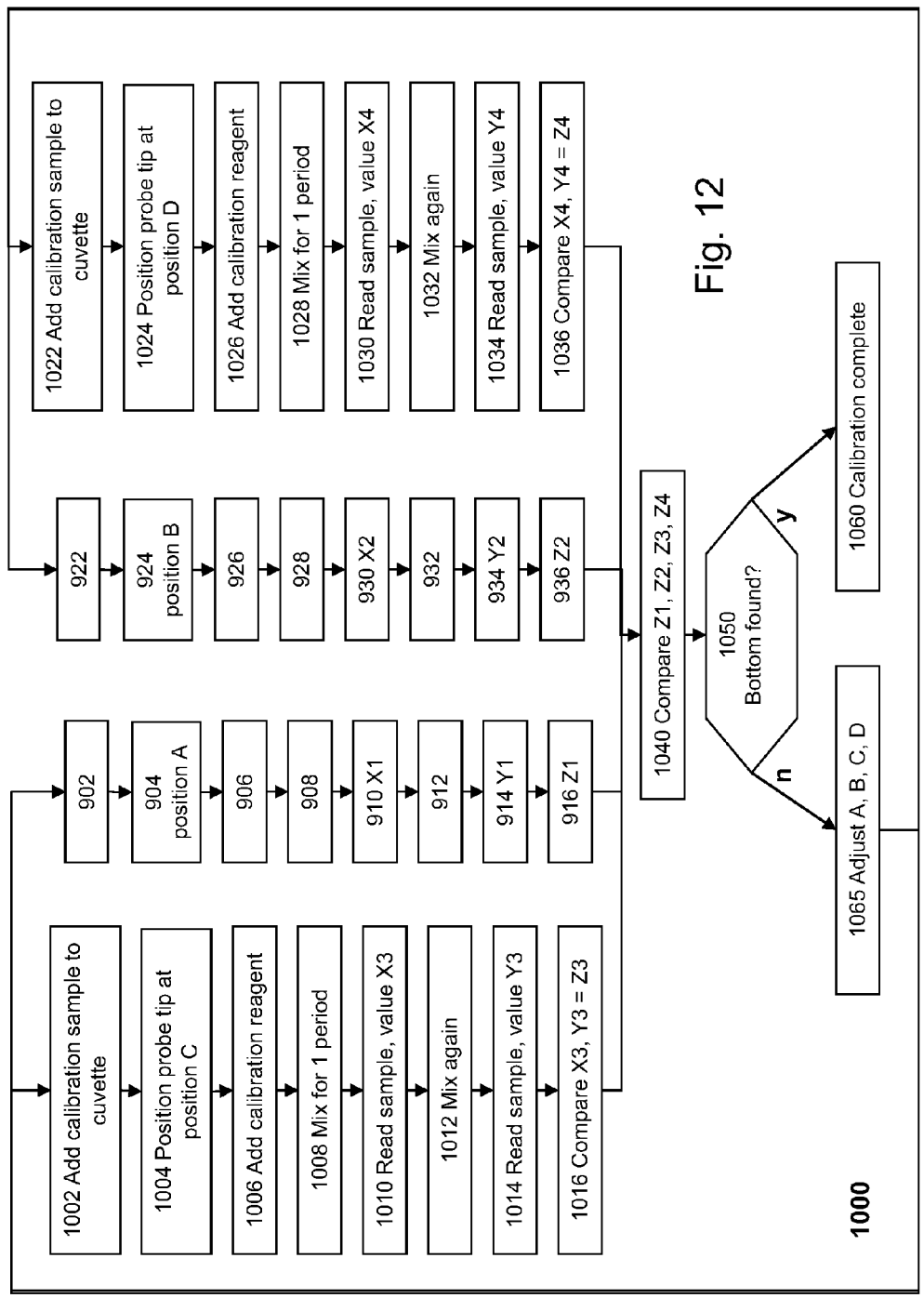
FIG. 12 is a flow chart showing an embodiment of the process for determining the proper alignment height of the tip of a probe needle.

It should be understood that method 900 may be employed at more positions than A and B, and that process 900 may be repeated until the bottom of a vessel is found. FIG. 12 shows an example of how more positions can be utilized. Method 1000 is an extension of method 900. Steps 902, 904, 906, 908, 910, 912, 914, 916, 922, 924, 926, 928, 930, 932, 934, and 936 are explained with respect to FIG. 9. As a result of these steps, values Z1 and Z2 are calculated for positions A and B, respectively. Steps 1002, 1004, 1006, 1008, 1010, 1012, 1014, and 1016 (which operate similarly to steps 902, 904, 906, 908, 910, 912, 914, and 916, respectively) calculate values X3, Y3, and Z3 for position C, which can be understood similarly to values X1, Y1, and Z1 of position A, respectively. Steps 1022, 1024, 1026, 1028, 1030, 1032, 1034, and 1036 (which operate similarly to steps 902, 904, 906, 908, 910, 912, 914, and 916, respectively) calculate values X4, Y4, and Z4 for position D, which can be understood similarly to values X1, Y1, and Z1 of position A, respectively. It should be understood with respect to method 1000 and method 900 that the value Y may not be necessary for each sample in some embodiments. For example, a single sample that has been completely mixed can be used to determine a value Y that can be used as value Y1, Y2, Y3, and Y4. Accordingly, steps 912, 914, 932, 934, 1012, 1014, 1032, and 1034 may be optional in some embodiments.

Positions A, B, C, D can be separated by the same or different distances. In some embodiments, position A is low, while position D is the highest vertical position. In some embodiments, the distance between adjacent positions is approximately ⅓ of a millimeter. In some embodiments, the distance between adjacent positions can be large during a first pass of method 1000, and can become smaller during subsequent passes of method 1002 to allow a coarse search and finer subsequent searches for the bottom of the vessel.

At step 1040, values Z1, Z2, Z3, and Z4 are compared to determine where the bottom of the vessel may be. Information at step 1040 may reveal that the bottom of the vessel is between any of the positions, or outside the range of these positions. The results may also reveal that the bottom of the vessel is substantially at one of the positions.

At step 1050, the result of the comparison at step 1040 determines if the bottom has been found. If the results are conclusive, calibration is complete at step 1060. If not, at step 1065, positions A, B, C, and D are adjusted. This can include choosing new positions that are outside the range of the existing positions A through D.

By utilizing the parallelism shown in the method 1000, a large range of vertical positions can be searched efficiently. Furthermore, by choosing four positions that are two steps apart, seven (rather than four) individual vertical steps can be evaluated simultaneously in a single pass of the method due to the known spatial relation between each tested position. Specifically, the results of the comparison 1040 can include: 1) conclusively identifying the location of the bottom, or 2) inferring that the bottom is above, below, or between any of all of the tested positions.

By knowing the spatial relation and comparing Z values of any two positions, the results can identify whether the position is at, above, below, or between those individual positions. For example, consider the potential outcomes from comparisons of the test results (Z1, Z2, and Z3) from tests at three positions A, B, and C with a spatial relationship from lowest to highest respectively. Comparing test results Z1 and Z2 from test position A and B, respectively, may reveal a difference that indicates that the bottom is between their respective test positions. Alternatively, if both the Z1 and Z2 results indicate that the bottom is above positions A and B, this information can also indicate that the bottom is substantially near position B by comparison to the result Z3 from a test position C, spatially above both A and B. In the case when the true bottom is substantially near position B, repeated evaluations at positions A and C would likely continue to test truly, that A is "below" and C is "above." However, the outcome Z2 from position B may be inconclusive or more correctly an intermediate outcome between the entirely-unmixed or entirely-mixed states of the probe-below or probe-above the true bottom respectively. Pairwise comparisons among repeated A and B, and B and C outcomes, result in a reasonable consensus interpretation that the bottom of the vessel is substantially near position B.

Figure 13:
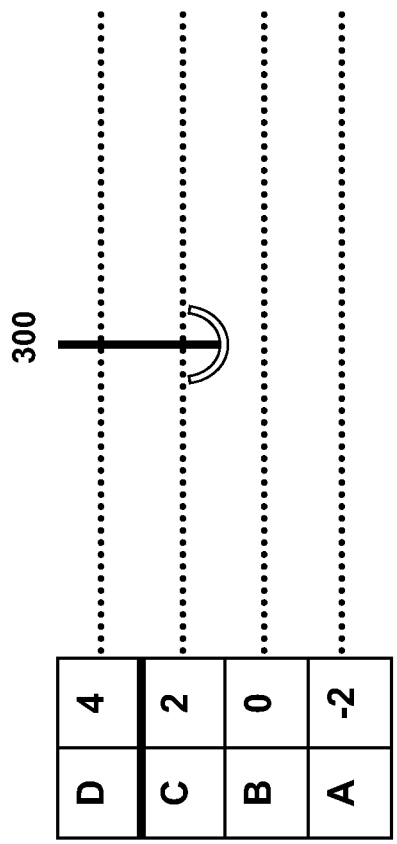
FIG. 13 is a logical diagram showing expected results for a given position of a cuvette when using the method of FIG. 12.

FIG. 13 shows an example where the true bottom of a vessel is between positions B and C. In this example, we describe the heights of these positions in steps from the initial assumed location of the bottom of the vessel. As shown in diagram 300, the initial assumed position of the bottom is at position B, which is indicated by the height offset of 0 steps. Meanwhile, position A is below position B at a height of −2. By convention, the sign of the numeric value for each position's step-number indicates the direction relative to the initial assumed location, 0. Negative position values are below the initial assumed location and positive position values are above. In this example, positions D and C are at +4 and +2 steps, respectively (above the initial assumed position). The true bottom of the vessel in this diagrammmed example is approximately 1 step above the intial assumed location for the bottom.

Table 302 shows the expected results when performing mixing tests at the various positions. At positions A and B, the result is a fully unmixed state, indicating that the probe is too low and in consistent contact with the bottom of the vessel. At positions C and D, the result is a fully mixed state, an indication that the probe is above the bottom. Table 304 shows the logical interpretation of comparisons A-B, B-C, and C-D. The result of A and B indicates that the probe should be raised. The result of C and D indicates that the probe should be lowered. Meanwhile, the result of B and C indicates that the bottom is between positions B and C.

Figure 14:
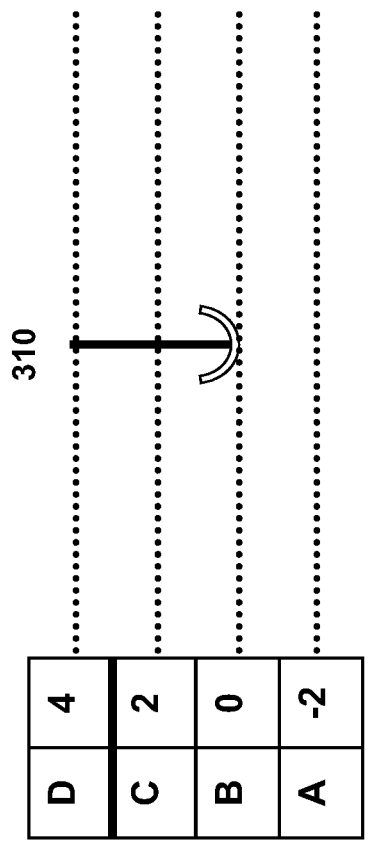
FIG. 14 is a logical diagram showing expected results for a given position of a cuvette when using the method of FIG. 13.

FIG. 14 shows an example where the true bottom of the vessel coincides with a tested location and, in this example, it coincides with the assumed initial position, position B. Test probe positions A through D are the same vertical locations as those detailed in FIG. 13. As shown in diagram 310, the location of the bottom is substantially at position B. Table 312 shows the results of mixing tests at the various positions. Attempts to mix with the probe at position A prevent any probe movement and leave the reaction entirely in an unmixed state. The consistent failure indicates that the actual bottom of the vessel is located above the tested location. Conversely, mixing attempts at the elevated positions C and D are free of any interference from contact with the bottom of the vessel and consistently produce a fully mixed state. The consistent and complete mixing indicate that the true bottom of the vessel is below these positions. Meanwhile, mixing at position B, which is substantially near the true bottom location of the cuvette, may produce an intermediate result due to the occasional contact with the bottom of the vessel during the duration of the test. The potential outcome of any one test at this position may range from a substantially unmixed state (<30%) to a substantially mixed state (>80%) or an intermediate value (between 30% and 80%). Table 314 shows the results of comparing the outcomes from the various pairs of positions. The CD pair consistently indicates that the probe tip is above the bottom of the vessel. Meanwhile, because the results from mixing at position B may be neither 0% (fully unmixed) nor 100% (fully mixed), individual results comparing A-to-B or B-to-C may be inconclusive. While a single stand-alone inconclusive/intermediate result at position B cannot be directly attributed to an interaction with the bottom of the vessel, the combined consistency of the outcomes from mixing tests at positions A and C that agree completely with their spatial arrangement validates the conclusion that the true bottom of vessel location is substantially near position B.

FIG. 15 shows a decision matrix that can be used to interpret the comparison of mixing results for four adjacent positions at step 1040 with known spatial arrangements ordered as follows: from A (lowest) next to B next to C next to D (highest). As shown in table 320, if the result of all comparisons is 1 (as shown in FIG. 11, state 206), it indicates that all tested positions were fully mixed and above the true bottom. If the result of all comparisons is −1 (as shown in FIG. 11, state 204), it indicates that all positions were substantially unmixed and below the true bottom (or possibly at position D). If one of the comparisons indicates a 0 (as shown in FIG. 11, state 202), it indicates that the bottom is found at the lower of the respective tested positions. If two adjacent comparisons indicate −1 and 1 in a spatially-meaningful relationship, the bottom is suggested to be between those respective tested positions. With the all-pair consesus indications that the bottom is below the lowest position or at or above the highest tested position, the target range of A-D can be adjusted accordingly.

Figure 16:
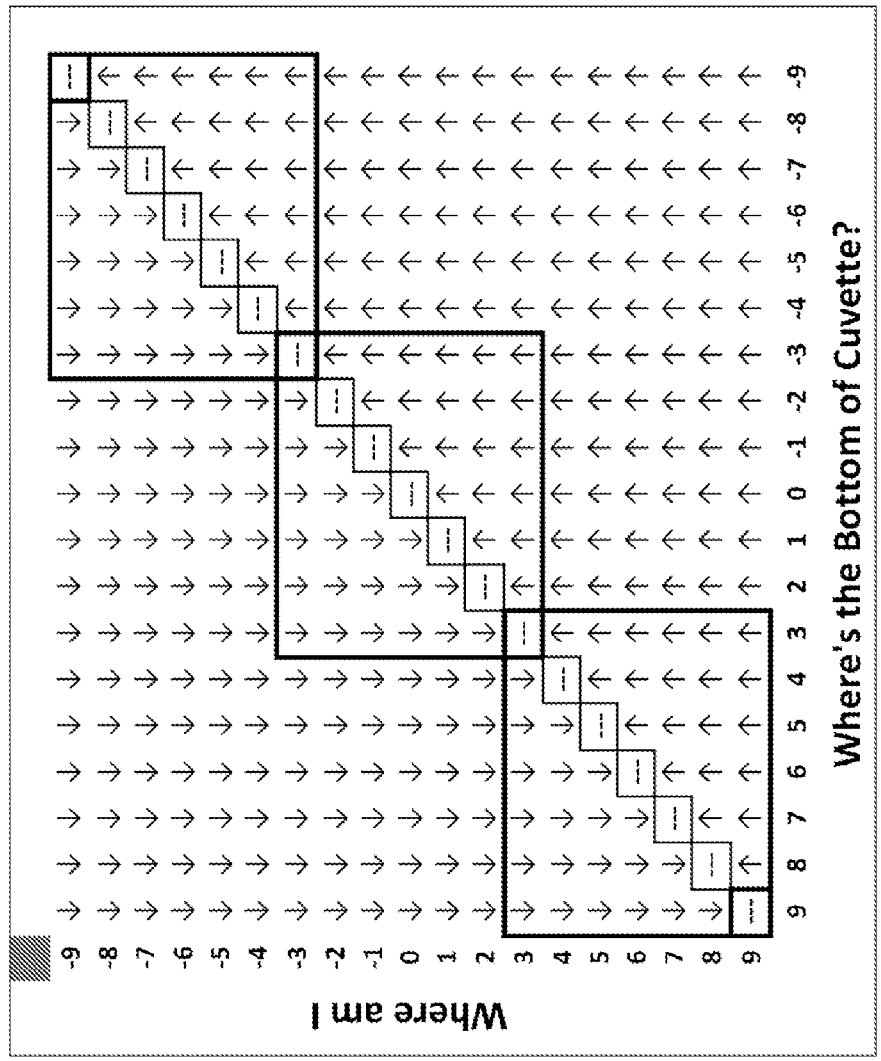
FIG. 16 is a logical mapping of the expected results determined by the spatial relations among all the combinations of various positions of the bottom of a vessel versus the various positions of a probe needle within the diagrammed space.

FIG. 16 shows a logical mapping of expected results for various positions of the bottom of a vessel and various positions of a probe needle. When the probe is at the various positions shown, the arrows indicate the direction of the bottom for each of the various possible locations of the bottom. The small boxes indicate when the probe location and bottom align. The larger boxes indicate the regions and the positions that three iterations of method 1000 will search by the basic test paradigm of a mix test at the target height compared to the result of a second mix test just above that height.

Figure 17:
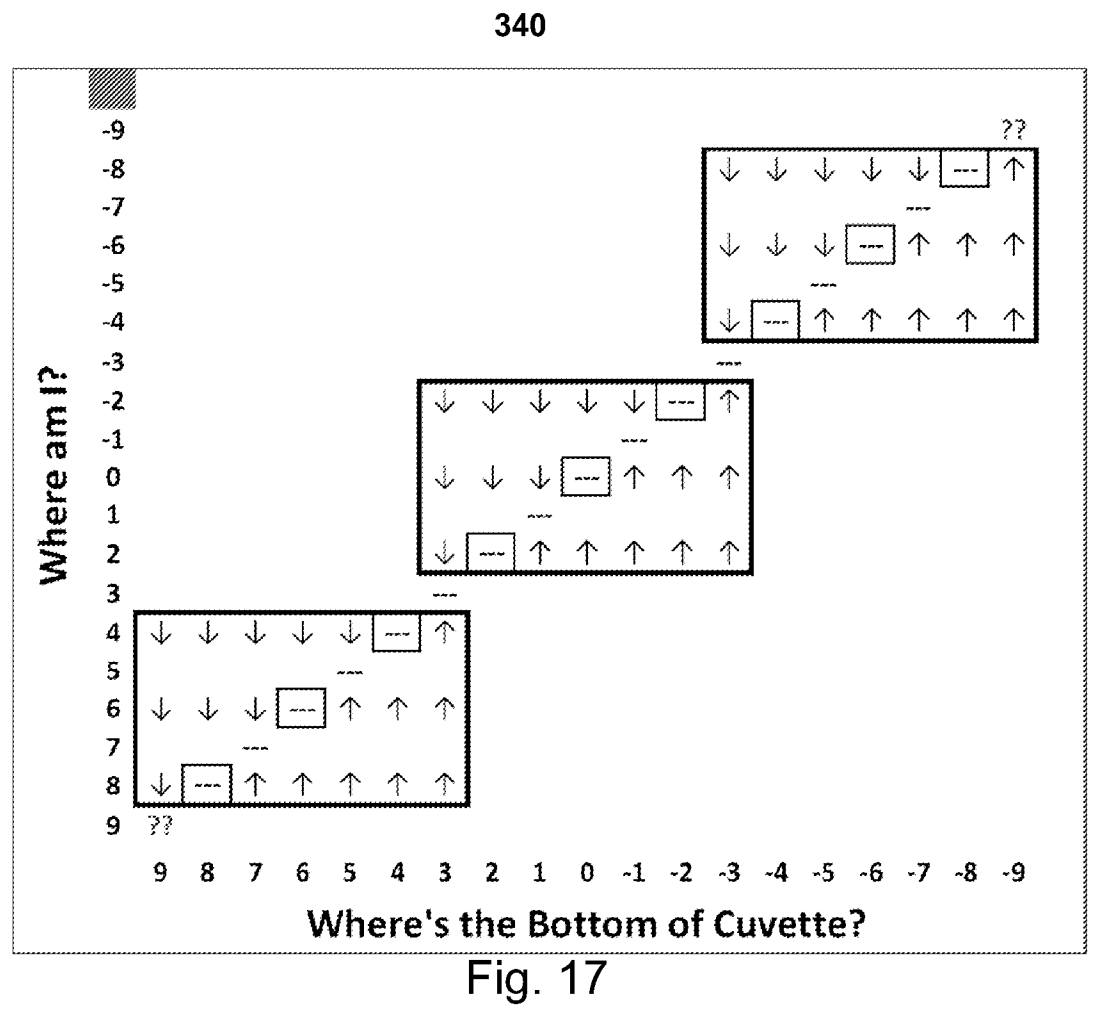

FIG. 17 shows possible results of three passes of method 1000. The diagram also illustrates how an initial search arrayed around the central (0,0) location provides information to indicate which second iteration, either higher or lower, would find the true bottom of cuvette location. It will be appreciated that certain lines are absent because adjacent test positions provide sufficient information to infer the outcome at that formally untested location. The three potential results from any position are 1) bottom is higher, 2) bottom is lower, or 3) bottom was found. When the tests are separated by two steps, this actual bottom can be found within the entire map of FIG. 16 with testing at only six positions.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A method for adjusting a position of a mixing element in an in vitro diagnostic apparatus, comprising:
   a) positioning the mixing element at a first vertical position in a first vessel having a first calibration sample;
   b) performing a first mixing test on the first calibration sample to determine a first value corresponding to a completeness of mixing at the first vertical position;
   c) positioning the mixing element at a second vertical position, above the first vertical position, in one of the first vessel or a second vessel;
   d) performing a second mixing test on a second calibration sample to determine a second value corresponding to a completeness of mixing at the second vertical position;
   e) comparing the first and second values to determine if a bottom of the first vessel is generally one of: at the first vertical position, below the first vertical position, above the second vertical position, and between the first and second vertical positions, wherein a vertical position is considered below the bottom of the first vessel if the bottom interferes with a tip of the mixing element when the mixing element is so positioned;
   f) mixing a plurality of patient samples with the mixing element at a third vertical position relative to the bottom if the bottom of the first vessel is between the first and second vertical positions;
   g) adjusting at least one of the first or second vertical positions; and
   h) repeating at least one additional mixing test until the comparing step indicates that the bottom of the first vessel is between the first and second vertical positions.

2. The method of claim 1, wherein the first and second vertical positions are separated by a predetermined step size.

3. The method of claim 1, further comprising: adjusting at least one of the first or second vertical positions in response to the comparing step, such that at least one vertical position is adjusted upward by a first increment if the bottom of the vessel is above the second vertical position and adjusted downward by a second increment if the bottom of the vessel is below the first vertical position.

4. The method of claim 3, wherein both the first and second vertical positions are adjusted.

5. The method of claim 3, wherein the adjusting step is repeated until an approximation of a vertical position of the bottom of the first vessel is determined.

6. The method of claim 5, further comprising positioning the mixing element at a third vertical position for mixing reagents during normal operation, wherein the third vertical position is a predetermined vertical offset above the approximation of the vertical position of the bottom.

7. The method of claim 5, wherein the first and second increments vary in magnitude in response to the comparing step.

8. The method of claim 7, wherein the first and second increments are reduced after successive comparing steps.

9. The method of claim 1, wherein at least one of the first and second mixing tests comprises the steps of:
   a) mixing the first or second calibration sample with the mixing element for a first predetermined time to create a first mixed state;
   b) measuring a property of the first mixed state;
   c) further mixing the first or second calibration sample with the mixing element for a second predetermined time to create a second mixed state;
   d) measuring a property of the second mixed state; and
   e) comparing the measurements of the first and second mixed states.

10. The method of claim 9, wherein the step of comparing the measurements of the first and second mixed states includes determining a ratio of a first measured value corresponding to the first state to a second measured value corresponding to the second state.

11. The method of claim 10, wherein the step of comparing the measurements of the first and second mixed states includes determining if the ratio exceeds a threshold value.

12. The method of claim 9, wherein at least a combination of the first and second predetermined time is great enough to mix the first or second calibration sample to a substantially complete mixed state when the mixing element is at a vertical position conducive to normal operation.

13. The method of claim 1, wherein the step (e) of comparing the first and second values further comprises determining if the bottom of the first vessel is adjacent the first or second vertical positions.

14. A method for adjusting a position of a mixing element in an in vitro diagnostic apparatus, comprising:
   a) positioning the mixing element at a first vertical position in a first vessel;
   b) depositing a first plurality of reagents in the first vessel in an unmixed state;
   c) moving the mixing element, during a first mixing step, in a horizontal mixing pattern to create a first mixed state of the first plurality of reagents;
   d) measuring a first value of a property of the first mixed state of the first plurality of reagents;
   e) performing a second mixing step, whereby the first plurality of reagents are further mixed to create a first substantially mixed state;
   f) measuring a second value of a property of the first substantially mixed state;
   g) comparing the first and second values corresponding to the first plurality of reagents to create a first result to determine a completeness of the first mixing step when the mixing element is at the first vertical position;
   h) positioning the mixing element at a second vertical position, above the first vertical position, in a second vessel, which may be the same as the first vessel;
   i) depositing a second plurality of reagents in the second vessel in the unmixed state;
   j) moving the mixing element, during a third mixing step, in the horizontal mixing pattern to create a first mixed state of the second plurality of reagents;
   k) measuring a first value of a property of the first mixed state of the second plurality of reagents;
   l) performing a fourth mixing step, whereby the second plurality of reagents are further mixed to create a second substantially mixed state;
   m) measuring a second value of a property of the second substantially mixed state;
   n) comparing the first and second values corresponding to the second plurality of reagents to create a second result to determine a completeness of the third mixing step when the mixing element is at the second vertical position;
   o) comparing the first and second results to determine if the second position is more effective at mixing samples than the first to estimate a location of a bottom of the first or second vessel;

p) mixing a plurality of patient samples with the mixing element at a third vertical position at a predetermined offset from the estimate of the location of the bottom; and q) adjusting the first and second vertical positions in response to step o.

15. The method of claim 14, further comprising repeating steps a) through q) until an approximation of a vertical position of a bottom of the vessel has been determined.

16. The method of claim 15, further comprising applying a predetermined vertical offset to the approximation of the vertical position of the bottom of the vessel during normal operation of a mixing process.

* * * * *